(12) United States Patent
Janson et al.

(10) Patent No.: US 7,320,872 B2
(45) Date of Patent: Jan. 22, 2008

(54) EPENDYMAL NEURAL STEM CELLS AND METHOD FOR THEIR ISOLATION

(75) Inventors: Ann Marie Janson, Stockholm (SE); Jonas Frisen, Stockholm (SE); Clas Johansson, Stockholm (SE); Stefan Momma, Spinga (SE); Diana Clarke, Cambridge, MA (US); Ming Zhao, Solna (SE); Urban Lendahl, Stockholm (SE); Kioumars Delfani, Solna (SE)

(73) Assignee: NeuroNova AB, Stockholm (SE)

( * ) Notice: Subject to any disclaimer, the term of this patent is extended or adjusted under 35 U.S.C. 154(b) by 734 days.

(21) Appl. No.: 10/183,728

(22) Filed: Jun. 27, 2002

(65) Prior Publication Data

US 2003/0092176 A1  May 15, 2003

Related U.S. Application Data

(63) Continuation of application No. 09/719,001, filed as application No. PCT/SE99/01157 on Jun. 24, 1999, now abandoned.

(30) Foreign Application Priority Data

Jun. 25, 1998  (SE) .................................... 9802264

(51) Int. Cl.
*G01N 33/567* (2006.01)
(52) U.S. Cl. ..................... 435/7.21; 435/368; 435/381
(58) Field of Classification Search ................ 435/368, 435/29
See application file for complete search history.

(56) References Cited

U.S. PATENT DOCUMENTS

| 5,753,505 A | 5/1998 | Luskin |
| 5,753,506 A | 5/1998 | Johe |
| 5,851,832 A | 12/1998 | Weiss et al. |
| 2003/0129747 A1 | 7/2003 | Frisen et al. |

FOREIGN PATENT DOCUMENTS

| WO | WO94/02593 | 2/1994 |
| WO | WO95/13364 | 5/1995 |
| WO | WO97/09885 | 3/1997 |
| WO | WO97/11716 | 4/1997 |
| WO | WO97/44442 | 11/1997 |
| WO | WO99/16863 | 4/1999 |

OTHER PUBLICATIONS

Vogel, Science, vol. 290 (2000) pp. 1672-1674.*
U.S. Appl. No. 09/104,772, filed Jun. 25, 1998, Frisen et al.
Date, 1996, Parkinson's Disease, Trophic Factors, and Adrenal Medullary Chromaffin Cell Grating: Basic and Clinical Studies, *Brain Research Bulletin* 40(1):1-19.
Goldman et al., 1998, Strategies utilized by migrating neurons of the postnatal vertebrate forebrain, *TINS* 21(3):107-114.
Hagan et al., 1997, "Parkinson's disease: prospects for improved drug therapy," *TiPS* 18:156-163.
McKay, 1997, "Stem Cells in the Central Nervous System," *Science* 276:66-71.
Mehta et al., 1997, "Neural Transplantation in Parkinson's Disease," *Can. J. Neurol. Sci.* 24:292-301.
Morrison et al., 1997, "Regulatory Mechanisms in Stem Cell Biology," *Cell* 88:287-298.
Reynolds and Weiss, 1992, "Generation of Neurons and Astrocytes from isolated Cells of the Adult Mammalian Central Nervous System", Science 255:1707-1710.
Lindsell et al., 1996, "Expression patterns of Jagged, Delta 1, Notch1, Notch2, and Notch3 genes identify ligand-receptor pairs that may function in neural development." Mol Cell Neurosci. 8(1):14-27.
Higuchi et al., 1995, "Differential expression of Notch1 and Notch2 in developing and adult mouse brain." Brain Res Mol Brain Res. 29(2):263-72.
Alvarez-Buylla A, Lois C., 1995, "Neuronal stem cells in the brain of adult vertebrates." Stem Cells. May;13(3):263-72. Review.
Alvarez-Buylla et al., 1998, "Primary neural precursors and intermitotic nuclear migration in the ventricular zone of adult Canaries." J Neurosci. 18(3):1020-37.
Weiss et al., 1996, "Multipotent CNS stem cells are present in the adult mammalian spinal cord and ventricular neuroaxis." J Neurosci. Dec. 1;16(23):7599-609.

* cited by examiner

*Primary Examiner*—James Ketter
(74) *Attorney, Agent, or Firm*—Jones Day

(57) ABSTRACT

The invention relates to an ependymal neural CNS stem cell, which cell expresses the surface protein Notch 1 together with at least one surface protein chosen from the group of Notch 2, Notch 3, CAR (transmembrane protein binding adenovirus) and CFTR cystic fibrosis transmembrane conductance regulator), and which cell also comprises at least one cilium. The invention also relates to preparations, including pharmaceutical preparations, comprising ependymal neural CNS stem cells, in vitro and in vivo assays based thereon and various other uses of the novel ependymal cells according to the invention.

26 Claims, 13 Drawing Sheets

G

EPENDYMAL NEURAL STEM CELLS AND METHOD FOR THEIR ISOLATION

This is a continuation of prior application No. 09/719,001 filed on Jul. 12, 2001, now abandoned which is the national phase under 35 U.S.C. § 371 of PCT International Application No. PCT/SE99/01157 which has an international filing date of Jun. 24, 1999, which designated the United States of America.

TECHNICAL FIELD

The present invention relates to a method of isolating ependymal neural CNS stem cells, that have never before been identified and isolated from the mammalian central nervous system. The invention also relates to preparations comprising such novel cells per se, pharmaceutical compositions containing the preparations, and to various medical uses thereof as well as assays using the same.

BACKGROUND

Until recent years, a 'static' view on the fate of nerve cells in the central nervous system (CNS) was universally prevailing, based on the assumption that new neurons could not be generated in the adult mammalian brain. However, such renewal of neurons has been described in certain regions of the adult CNS, e.g. in the olfactory bulb, where signals from neurons from the organ of smell reach the brain (Kaplan et al., Science 197:1092) and in the dentate gyrus of hippocampus (Bayer et al., Science 216:890). Since neurons are unable to divide, the addition of new neurons suggested the existence of immature cells, i.e. progenitor or stem cells, which may generate neurons. Evidence supporting the existence of a multipotent neural stem cell in the adult mammalian CNS was presented a few years ago (Reynolds et al., Science 255:1707). However, as in several other organs, the realisation of the existence of a stem cell has come before identifing and localising the same. Interestingly, neurogenesis in the adult brain persists throughout adulthood in rodents (Kuhn PG, J. Neurosci. 16:20) and seems to be an evolutionary well conserved phenomenon present in a variety of mammals (Gould et al. J. Neurosci. 17:2492, Gould et al., Proc. Natl. Acad. Sci. USA 95:3168). In humans, the issue is difficult to address, although experimental data from cultures of adult human brain tissue (Kirschenbaum et al, Cereb. Cortex 6:576) suggest that there may be continuous neurogenesis also in the adult human CNS.

The existence of neural stem cells in the adult mammalian CNS was first demonstrated by culturing cells from the adult rat brain and spinal cord. Under certain culture conditions a population of multipotent neural stem cells can be propagated from dissociated adult rat brain and spinal cord (Reynolds et al., Science 255:1707, Dev. Biol. 175:1, Weiss et al., J. Neurosci. 16: 7599). The culture medium has to contain a mitogenic factor, e.g. epidermal growth factor (EGF) or fibroblast growth factor (FGF), and serum must be excluded. In contrast to stem cells, most other CNS cell types do not survive in these cultures.

Under these conditions, single cells proliferate in vitro and the progeny forms a cluster of aggregated cells (Reynolds et al., Science 255:1707, Dev. Biol. 175:1). Such cell clones detach from the culture dish after a few days in vitro. The cells continue to proliferate and form a characteristic spheroid cell aggregate, referred to as a neurosphere, of tightly clustered cells, all of which are derived from a single cell. Most of the cells in the neurosphere express nestin (Lendahl et al., Cell, 60:585), but not markers typical for differentiated cells. These undifferentiated cells rapidly differentiate if plated on an adhesive substrate or if serum is added to the culture medium. Importantly, a clone of cells derived from a single cell can generate neurons, astrocytes and oligodendrocytes, demonstrating that at least the initial cell was multipotent (Reynolds et al., Science 255:1707, ibid. Dev. Biol. 175:1). Moreover, if a cell clone is dissociated, many of the cells will form new clusters of undifferentiated multipotent cells (Reynolds et al., Dev. Biol. 175:1), thus fulfilling the criteria for being stem cells.

Thus, the method above suffers from the serious drawback that the cell population used is of a complex, mixed composition. Even though it has been possible to enhance the growth of some cell types, it is impossible to draw any conclusions regarding the original localisation of the cells obtained.

Consequently, other methods have been proposed to determine the localisation of the adult CNS stem cells, wherein different parts of the adult rodent forebrain have been carefully dissected and cultured to test for the capacity of neurogenesis. These studies have demonstrated that stem cells are most abundant in the wall of the lateral ventricle and in the hippocampus (Lois et al., Proc. Natl. Acad. Sci. USA, 90:2074, Morsehead et al., Neuron 13:1071, Palmer et al., Mol. Cell. Neurosci. 6:474, ibid, 8:389). Furthermore, stem cells can be isolated from the walls of the third and fourth ventricles as well as from the adult spinal cord, suggesting the presence of stem cells adjacent to the ventricular system along the entire neuraxis (Weiss et al., J. Neurosci. 16: 7599).

However, the exact localisation and identity of the neural stem cell has been enigmatic. The wall of the lateral ventricles has been the subject of detailed morphological studies (Doetsch et al., J. Neurosci. 17:5046). The ventricular system is lined by a single layer of ependymal cells. Mammalian ependymal cells have traditionally been considered to be highly specialised cells with the main function to form a barrier between the nervous tissue and the cerebrospinal fluid (Del Bigio, Glia 14:1), which strongly argues against these cells being undifferentiated stem cells. Beneath the ependymal layer is the subependymal layer, also known as the subventricular zone. This area harbours astrocytes, neuroblasts and progenitor cells (Doetsch et al., J. Neurosci. 17:5046). The progenitor cells in the subependymal layer have a high proliferation rate (Morsehead et al., J. Neurosci. 12:249). Generally, stem cells proliferate very slowly and when the rapidly proliferating subependymal cells were selectively killed, the stem cell population was not depleted, arguing against these cells being the stem cells (Morsehead et al., Neuron 13:1071).

WO 97/44442 (Johe) discloses the isolation of stem cells from the CNS of mammals and more specifically from the subependymal region of striatum lining the lateral ventricles. However, only subependymal cells are used and thus there is no further teaching regarding the identity and role of mammalian ependymal cells that alters the conventional one.

WO 95/13364 (Weiss et al.) relates to a method of proliferation of CNS precursor cells located by the CNS ventricle of a mammal. However, only precursor cells are disclosed, and there are no teachings as regards other cell stages, such as stem cells.

In this context, it is interesting to note that besides the olfactory bulb and the hippocampus, data on continuous neurogenesis throughout adulthood in other regions of the mammalian brain have been scarce. As an example that neurogenesis may be a more widespread phenomenon, a small number of cells with the capacity to generate neurons in vitro has been isolated from the striatum and septum (Palmer et al., Mol. Cell. Neurosci. 6:474), although it has not been tested if these cells have stem cell properties or if they are committed neuronal progenitors.

There is increasing evidence that nervous system injuries may affect stem cells in the adult CNS. After both spinal cord and brain injuries, nestin expression is increased in cells lining the central canal and in the subventricular zone, respectively (Frisen et al., J. Cell Biol. 131:453, Holmin et al. Eur. J. Neurosci. 9:65). These cells have been suggested to derive from stem cells. With time, nestin expressing cells are seen progressively further from the central canal and the lateral ventricle and these cells express astrocytic markers (Frisen et al., J. Cell Biol. 131:453, Holmin et al. Eur. J. Neurosci. 9:65). These data have lead to the suggestion that stem cells or progenitor cells residing by the ventricular system are induced to proliferate, migrate toward the site of the injury and differentiate to astrocytes. Furthermore, hippocampal lesions increase the proliferation of hippocampal progenitor cells and the number of granular neurons in the hippocampus (Gould et al. Neurosci. 80:427). However, since the stem cell has not been identified or exactly localised it is not clear whether stem cells play a role in Injury processes.

Doetsch et al., Cell 97:703, have recently tried to analyse the identity of a neural stem cell in the wall of the lateral ventricle of the adult brain. They provide several experiments suggesting that a stem cell express glial fibrillary acidic protein (GFAP). GFAP is expressed in many astrocytes and Doetsch et al conclude that the stem cell they describe is an astrocyte. However, there is a plethora of studies by them and other groups unequivocally demonstrating that GFAP is expressed in several other cell types, such as certain liver cells, non-myelinating Schwann cells, tanycytes and ependymal cells. This makes it impossible to conclude, based on GFAP expression, that the stem cell they describe is an astrocyte. No astrocyte-specific marker has been demonstrated to be expressed by neural stem cells by Doetsch et al or any other group.

WO 99/16863 discloses generation of hematopoietic cells from mammalian multipotent neural stem cells. Accordingly neural stem cells can be administrated to patients having leukemia, lymphoma or immune deficiency instead of a bone marrow transplantation. However, the document is completely silent regarding regeneration of other organs.

Accordingly, the discovery of the existence of neural stem cells in the adult CNS of mammals is important and may make it possible to develop strategies to stimulate generation of new neurons or glial cells. However, several important questions have remained unanswered and better methods to culture these cells and to study them quantitatively in vivo are needed. Most importantly, it is absolutely vital to identify and localise the stem cell in the adult CNS in order to be able to study these cells further and to stimulate generation of new neurons from the stem cells.

Furthermore, there are no methods available today to purify stem cells at an early step in tissue culture. Although there are several general methods available for purifying cell populations in other tissues, it is impossible to utilize these methods, or to develop new methods, without knowledge of the true identity of the stem cell. Further studies of a better defined cell population are required for screening of pharmaceutical compounds. Moreover, the development of quantitative methods to label and follow the stem cells and their progeny in vivo to allow detailed studies of for example regulation of the generation of new neurons to analyse the effect of different chemicals or genetically manipulate the stem cells are needed. Again, although there are methods known in the art that can be used to follow other cell populations in vivo, it is impossible to utilize these methods or develop new methods for following stem cells since the identity of the stem cell has been unknown. The development of quantitative methods to follow stem cells and their progeny in animal models of neurodegenerative disorders and injuries of the CNS would open up the possibility to screen new treatment strategies in human conditions where today only some of the symptoms, but not the neuronal loss per se, can be alleviated.

Thus, a problem within this field is that even though neural stem cells are known to exist, the localisation and identity thereof is not known. Could this be accomplished, a great step forward would be taken by research aimed at providing the above defined goals.

SUMMARY OF THE INVENTION

The object of the present invention is to solve the above defined problem. This is achieved according to the present invention by identifying the origin and identity of neural stem cells and by selectively isolating such stem cells from CNS tissue. The invention thus resides in the surprising discovery that cells found in the ependymal layer are neural stem cells. Thus, the present invention provides an ependymal neural CNS stem cell as defined in claim 1. The invention also provides a method of isolating such ependymal neural CNS stem cells from the ependymal layer. Accordingly, for the first time ever, the actual identity and localisation of neural stem cells are disclosed herein, thus enabling various advantageous uses and applications thereof within the medical and diagnostic field. The invention also relates to in vitro and in vivo assays as well as pharmaceutical compositions, wherein the new findings according to the invention are advantageously employed.

DEFINITIONS

Figure 1:
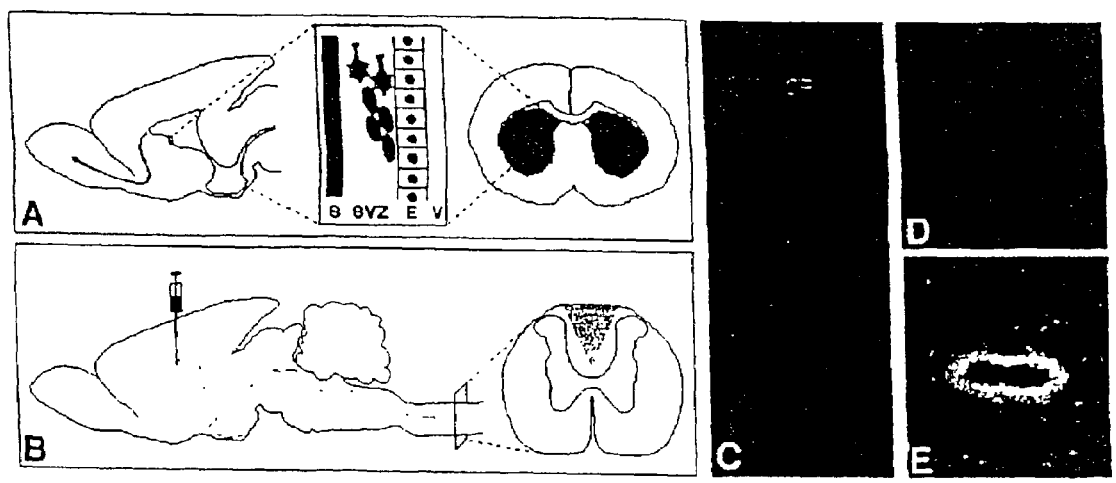
FIG. 1 illustrates the specific labelling of ependymal cells and is a schematic drawing of the migration of neurons in the adult forebrain and the structure of the wall of the lateral ventricle.

In the present context application, the term "isolated" refers to cell fractions isolated from an animal or a human and purified up to at least about 10%, preferably at least about 30%, more preferably at least about 50% and most preferably at least about 60%, such as about 80%. In a particular embodiment of this aspect of the invention, the purity of the isolated cells is close to 100%, such as about 90%. In such a cell population having a purity of about 90%, perhaps only about 4% of the stem cells clearly act as "active" stem cells but the rest of the stem cells are quiescent although they may have the ability to be transformed into such "active" stem cells. An "active" stem cell is defined as a cell that undergoes self-renewal and is multipotent. The term "neural stem cells" relates to cells capable of generating aggregates of undifferentiated cells, so called neurospheres, under suitable conditions, e.g. a medium containing appropriate mitogens. "Ependymal cells" refers to any cell residing partly or completely in the ependymal layer in the CNS ventricular system or the same cell type located elsewhere. An "ependymal cell" is defined herein to include any cell having the characteristics of an ependymal cell isolated from the ependymal cell layer of post-natal CNS tissue. In the present context, it is to be understood that the feature that characterise the stem cells according to the invention is the capability thereof to generate new stem cells, precursors, or progenitor cells as well as new neurons, astroglia, or oligodendroglia.

Ependymal neural stem cells also express some specific cell surface markers that can be used for isolation and identification purposes, such as Notch1 (transmembrane receptor), Notch2, Notch3, CAR (transmembrane protein binding adenovirus, Tomko et al., Proc Natl Acad Sci USA, 94:3352) and CFTR (cystic fibrosis transmembrane conductance regulator, Kunzelmann Rev. Physiol. Biochem. Pharmacol. 137:1). Ependymal neural CNS stem cells also comprise at least one cilium. The term "adult" is used herein to differentiate the neural stem cells previously identified in embryos from the present neural stem cells obtained from post-natal mammals. Thus, adult stem cells are in essence non-embryonic stem cells.

For the purposes of the present invention, dissociation of ependymal tissue can preferably be carried out using one or a combination of dissociation enzymes chosen from the group of collagenase, trypsin and hyaluronidase, as well as kynurenic acid. Ependymal tissue can also be dissociated by mechanical dissociation, either alone or in combination with one or more of the above mentioned enzymes.

DETAILED DESCRIPTION OF THE INVENTION

The invention relates to an adult neural CNS stem cell being an ependymal stem cell, in other words a neural stem cell residing in the ependymal layer. The invention thus provides neural stem cells, which may be characterised by possessing the characteristics of an ependymal cell. More specifically, in a first aspect, the present invention relates to an ependymal neural CNS stem cell, which cell expresses the surface protein Notch1 together with at least one surface protein chosen from the group of Notch2, Notch3, CAR (transmembrane protein binding adenovirus) and CFTR (cystic fibrosis transmembrane conductance regulator), and which cell also comprises at least one cilium.

In a second aspect, the present invention relates to a method of isolating ependymal neural CNS stem cells from adult or post-natal CNS tissue, which method preferably comprises dissociating ependymal tissue and recovering said ependymal neural CNS stem cells therefrom. Said dissociation may be performed by any suitable method easily chosen by someone skilled in this field. The cells are recovered by separation by any suitable technique from any undesired material present, the amount and quality of which will vary depending on the procedure used for obtaining the tissue as well as the condition thereof.

This aspect of the invention thus relies upon isolating a particular cell type from the post natal CNS tissue. The person skilled in the art would readily understand that this may be achieved in various ways. Thus, for example as above, the ependymal cell layer could be dissected out from the neural tissue and subsequently processed to isolate ependymal cells therefrom. Thus, ependymal tissue may selectively be dissociated and ependymal stem cells isolated or recovered therefrom.

Alternatively, ependymal stem cells may selectively be isolated from a CNS tissue preparation, which may comprise heterogeneous tissue types. Thus, for example, a larger region of brain tissue, which may contain tissues other than the ependymal cell layer, may be dissected and ependymal cells may selectively be isolated therefrom, for instance by recovering only cells having ependymal cell characteristics. As will be discussed in more detail below, this may be achieved by, for example, using affinity separation techniques with affinity reagents having specificity for cell surface markers specific for ependymal cells.

Thus, the ependymal stem cells are dissociated, preferably to single cells, and then separated. This is provided by screening the cells obtained by the method for cells exhibiting at least one characteristic or trait of an ependymal neural stem cell. Neural stem cells from adults have been disclosed in the prior art and the skilled in this field will decide on optimal screening methods for the prevailing conditions.

In an advantageous embodiment of the present method, the tissue is collected from the ependymal layer of the walls of the ventricular system of the brain or spinal cord of said human or animal. Such a dissection and recovery of tissue is easily performed by the skilled man in this field by any suitable routine method. The dissociation step is performed by any suitable method, such as an enzymatic and/or mechanical treatment, and is not restricted in any way as long as the desired single cells are obtained as a result thereof. Examples of such methods are e.g. trituration, trypsin treatment, collagenase treatment and hyaluronidase treatment. Most preferably, the dissociation is performed by enzymatic treatment with trypsin. The dissociation of tissue may alternatively be performed by any other method easily chosen by the skilled man in view of the prevailing conditions.

The screening of the resulting cells, such as single cells, is as mentioned above performed by any suitable method depending on the characteristic, trait or property of an ependymal cell used. In one embodiment of the present method, the screening is performed by use of the expression of a specific cell surface marker, such as a protein. Such an expression of a surface protein may for example be the expression of the Notch1, Notch2 and/or Notch3 receptors, which have previously been disclosed in the literature but in other contexts. In the most preferred embodiment of this method, the single cells are screened for their expression of the Notch1 receptor. In an alternative embodiment of this aspect of the invention, the single cells are screened for using previously labelled ependymal cells. Such a labelling may be a dye and is advantageously a fluorescent labelling, such as DiI, as shown in example 1. DiI has also been disclosed in other contexts and is well known to the skilled in this field. The labelling of cells is used extensively within research and in diagnostic methods and the choice of a suitable technique is thus easily made by the skilled man. In an alternative embodiment, a virus, such as an adenovirus or a lentivirus may be used.

In a further aspect, the invention relates to a preparation comprising ependymal neural CNS stem cells. Such a preparation can be obtained by any of the isolation methods disclosed herein. Such preparations comprise at least about 10%, such as 10-50%, e.g. about 35%, or in the preferred embodiment, up to about 90%, or most preferably an essentially pure culture, of neural stem cells. Preferably, at least about 4% of these cells are fully active stem cells. Naturally, much higher concentrations are possible to obtain, depending on the screening method chosen. Previously, in prior art procedures, parts of a brain have been dissociated and specific growth factors have been added in order to induce growth of a specific cell type. Such procedures may have generated relatively high concentrations of cells in the end, however, that is after several days of growth. Most importantly, such procedures have never been aimed at obtaining a pure population of stem cells at an early step in the culture procedure, since the identity and characteristics (for example expression of specific cell surface markers) of the stem cell have been unknown before the present invention. Thus, in practice, the present method yields the desired concentration of a cell type, i.e. the ependymal stem cells disclosed herein, that has never been identified and/or localised before. In a specific embodiment, the product consists of about 90-95% of ependymal neural stem cells. In one advantageous embodiment, the product of the method is a cell fraction consisting almost entirely, that is, of about 100%, of the ependymal neural stem cells. Accordingly, the present invention also relates to isolated neural stem cells obtainable by the method according to the present invention as well as to any fraction of isolated neural stem cells.

In another aspect, the ependymal neural stem cells prepared by the present method can be genetically modified. Manipulations may be performed in order to modify various properties of the cell, e.g. to render it more adapted or resistant to certain environmental conditions, to induce a production of one or more certain substances therefrom, which substances may e.g. improve the viability of the cell or alternatively may be useful as drugs or medicaments. Further details regarding the possibilities and advantages of such manipulated cells according to the invention are provided below, in the section "Discussion". Some such genetic alterations may be performed in order to make the cell more suitable for use in transplantation, for example, in order to avoid rejection thereof from the recipient (for reviews of gene therapy procedures, see Anderson, *Science* 256:808; Nabel and Felgner TIBTECH 11:211; Mitani and Caskey *TIBTECH* 11:162; Mulligan Science 926; Dillon TIBTECH 11:167; Miller Nature 357:455; Van Brunt Biotechnology 6(10):1149; Vigne *Restorative Neurology and Neuroscience* 8:35; Kremer and Perricaudet British Medical Bulletin 51(1) 31; Haddada et al. in *Current Topics in Microbiology and Iminunology*, Doerfler and Böhm (eds.) Springer-Verlag, Heidelberg Germany; and Yu et al., Gene Therapy 1:13). Thus, the present invention also encompasses gene therapy methods, wherein neural stem cells are used as well as preparations intended to be used in such methods comprising the cells according to the invention. Such gene therapy methods may be used to treat and/or prevent any conditions wherein the neurons or glia in the CNS have been impaired or are defect.

In another aspect, the present invention relates to a composition comprising neural stem cells for use in therapy e.g. as a medicament. In addition, the invention also relates to the use of a neural stem cell in the preparation of a therapy, e.g. a medicament, for regulating the neurogenesis or gliogenesis in the central nervous system, such as the brain. Such regulation is either inducing or inhibiting and the treatment may be aimed at Parkinson's disease, Alzheimer's disease, stroke, trauma etc. In the case of glial cells, the medicament may be intended for treating Multiple Sclerosis and other glia related conditions. These compositions could also be used in generation of other tissues such as the myocardium comprising the atrial and ventricular walls of the heart, the dorsal aorta, and the genital ridge primordium and mesonephric tubules. Other examples of organs that could be generated are the optic stalk, retinal layer and lens of the eye, the inner ear, the liver, pancreas and other endocrine organs. In one particular embodiment of the invention, these aspects of the invention use neural stem cells obtained by the method disclosed above, even though the invention also encompasses the uses of any neural stem cells, such as genetically modified neural stem cells, for the present purposes.

Accordingly, the invention relates to a pharmaceutical preparation comprising at least one ependymal neural stem cell according to the invention and a pharmaceutically acceptable carrier. The preparations according to the invention may be adapted for injection into a suitable part of the central nervous system. Such a pharmaceutical preparation comprises any suitable carrier, such as an aqueous carrier, e.g. buffered saline etc. The active composition of the present preparation is generally sterile and free of any undesirable matter. In addition, the preparations may contain pharmaceutically acceptable auxiliary substances as required to approximate physiological conditions, such as pH adjusting agents etc. The concentration of the present neural stem cell in the preparation will vary depending on the intended application thereof and the dosages thereof are decided accordingly by the patient's physician. The stem cells used may have been isolated by the present method or any other suitable method or obtained in any other way. In a preferred embodiment, the present stem cell may have been genetically manipulated in order to be especially adapted for the intended use thereof.

In a further aspect, the cells of the invention can be administered to a patient wherein such administration is therapeutically useful. Alternatively, the cells of the invention can be used to replace or supplement the corresponding cell type in a patient by administration of the cells of the invention. The cells of the invention may be used to coat implants, thus acting as a barrier between the implant and the patient. Administration of the cells of the invention is achieved by methods known to those skilled in the art.

In a further aspect, the present invention also relates to an animal, such as a mouse, which comprises a genetically modified ependymal neural stem cell according to the invention. Such animals may e.g. be useful as models in research or for testing of new drugs.

In yet a further aspect, the present invention relates to the use of the present neural stem cells as "drug targets", preferably in in vitro assays, to stimulate stem cells to generate a particular neuronal phenotype or glial subtype. In a particular embodiment, the invention relates to the use of said cells in the culture in vitro of new neurons. Such a use may e.g. involve culturing of isolated neural stem cells, as is disclosed in more detail in the section "Discussion" below. The present invention also relates to the substances obtained by the use defined above.

In another aspect, the present invention relates to an unbiased quantitative or qualitative, preferably quantitative, method to assess neurogenesis and migratory streams of stem cell progeny, preferably in in vivo assays, in various regions of the brain as well as techniques to analyse the total number of stem cells and their progeny migrating to various regions of the brain. This is for the development of new screening methods, which methods are also within the scope of the present invention as defined by the appended claims. This could be of use in diagnosing patients suffering from neurodegenerative diseases, if the development of ependymal cell markers suitable for positron emission tomography (PET), or other imaging systems able to visualise the living brain with sufficient resolution, allows the diagnosis of defective migration and/or differentiation of the stem cell progeny in human CNS. Thus, the present invention also relates to kits and assays for performing such methods as well as to substances obtained by the present methods.

In a last aspect, the present invention relates to a method of treating a human or animal patient suffering from a neurodegenerative disease, which method comprises the administration to said human or animal of a pharmaceutically effective amount of ependymal neural stem cells. In general, such a method is based on administration of ependymal stem cells according to the invention with an unimpaired function and ability to produce neurons or other cell types depending on the human CNS disorder. Alternatively, neurons or glial cells generated from stem cells in vitro can be administrated to the CNS. In an alternative embodiment, the invention relates to a method of treatment and/or prevention of neurodegenerative disorders in a human or animal patient, wherein the existing defective neural stem cells' ability to produce new neurons or migrate to the appropriate target is restored. Such a method is based on the administration of a substance that stimulates and induces the neural stem cells' native properties and capability to produce neurons. Alternatively, such a method may be based on the administration of a substance that actually inhibits the degenerative process of the neurons.

Accordingly, the cells of the present invention can be transplanted into a patient for the treatment of disease or injury by any method known in the art which is appropriate for the transplant site.

Methods of administration of the cells of the invention include but are not limited to intradermal, intramuscular, intraperitoneal, intravenous, subcutaneous, intranasal, and epidural routes. The cells of the invention may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the cells of the invention into the central nervous system by any suitable route, including intraventricular and intrathecal injection; intraventricular injection may be facilitated by an intraventricular catheter, for example, attached to a reservoir, such as an Ommaya reservoir.

It may be desirable to administer the cells of the invention locally to the area in need of treatment; this may be achieved by, for example, and not by way of limitation, local infusion during surgery, topical application, e.g., in conjunction with a wound dressing after surgery, by injection, by means of a catheter, or by means of an implant, said implant being of a porous, non-porous, or gelatinous material, including membranes, such as sialastic membranes, or fibers.

The following describes exemplary methods which can be modified for the transplantation of transformed cells: Protocols for the isolation and transplantation of fetal tissues in humans have been reported and clinical trials involving these studies having been carried out. For example, Lindvall, Science 247:574, have described results regarding grafts and survival of fetal dopamine neurons after transplantation into brain. Rinsing and partial dissociation of precursor cells, if necessary, can be carried out by a modification of the protocol described in Lindvall, Arch. Neurol. 46:615.

By way of example, implantation of cells into the brain can be performed as follows. Implantation is done at three sites in the left putamen with a stereotactic technique (Lindvall, Arch. Neurol. 46:615). For each site, 20 æl of the dissociated cells is drawn into the instrument (outer diameter, 1.0 mm). The cells are injected along a 10, 12 and 14 mm linear tract, respectively, in either 2.5 æl portions for 15 to 20 seconds each. Between each injection there is a 2 minute delay, and the cannula is then retracted 1.5 to 1.7 mm. After the final injection, the cannula is left in situ for 8 minutes before being slowly withdrawn from the brain. After surgery the cell viability is assessed following the procedure of Brundin, Brain. Res. 331:251.

Another example is outlined by Caplan et al., 1993, U.S. Pat. No. 5,226,914. Briefly, after marrow cells are harvested from bone marrow plugs and the marrow mesenchymal, stem cells are separated by centrifugation. The stem cells are isolated further by selective adherence to the plastic or glass surface of a tissue culture dish. The stem cells are allowed to proliferate but not differentiate. Porous ceramic cubes composed of 60% hydroxyapatite and 40% -tricalcium phosphate are added to the cells under a slight vacuum. The cubes with adhered cells are implanted into incisional pockets along the backs of nude mice. The mesenchymal stem cells differentiate into bone.

The titer of cells transplanted will be effective in the treatment of a particular disorder or condition will depend on the nature of the disorder or condition, and can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances.

The invention also provides a pharmaceutical pack or kit comprising one or more containers filled with one or more of the ingredients of the pharmaceutical compositions of the invention and/or reagents to prepare the pharmaceutical compositions of the inventions. Optionally associated with such container(s) can be a notice in the form prescribed by a governmental agency regulating the manufacture, use or sale of pharmaceuticals or biological products, which notice reflects approval by the agency of manufacture, use or sale for human administration.

The cells of the invention may also be maintained in culture for use in research, including medical research. For exanple, the cells may be used for screening test compounds of compounds with known function for their ability to differentiate the cells of the invention into different cell types.

DETAILED DESCRIPTION OF THE DRAWINGS

FIG. 1: Specific Labelling of Ependymal Cells

Schematic drawing of the migration of neurons in the adult forebrain and the structure of the wall of the lateral ventricle (A). The ventricle (V) is lined by ependymal cells (E). Between the ependymal layer and the striatum (S) is the subventricular zone (SVZ), where precursor cells (light blue) divide to give rise to immature neurons (dark blue). The neurons migrate to the olfactory bulb (blue arrow). (B) Labelling of ependymal cells. DiI is injected stereotaxically into a lateral ventricle, resulting in labelling of ependymal cell throughout the ventricular system. In some of these animals, an incision (grey area in the spinal cord cross section) was made in spinal cord dorsal funiculus. The DiI injection labels the ependymal layer lining the lateral ventricle (C, D) and the spinal cord central canal (E) six hours after the injection. The choroid plexus (CP) is labelled in (C).

Figure 2:
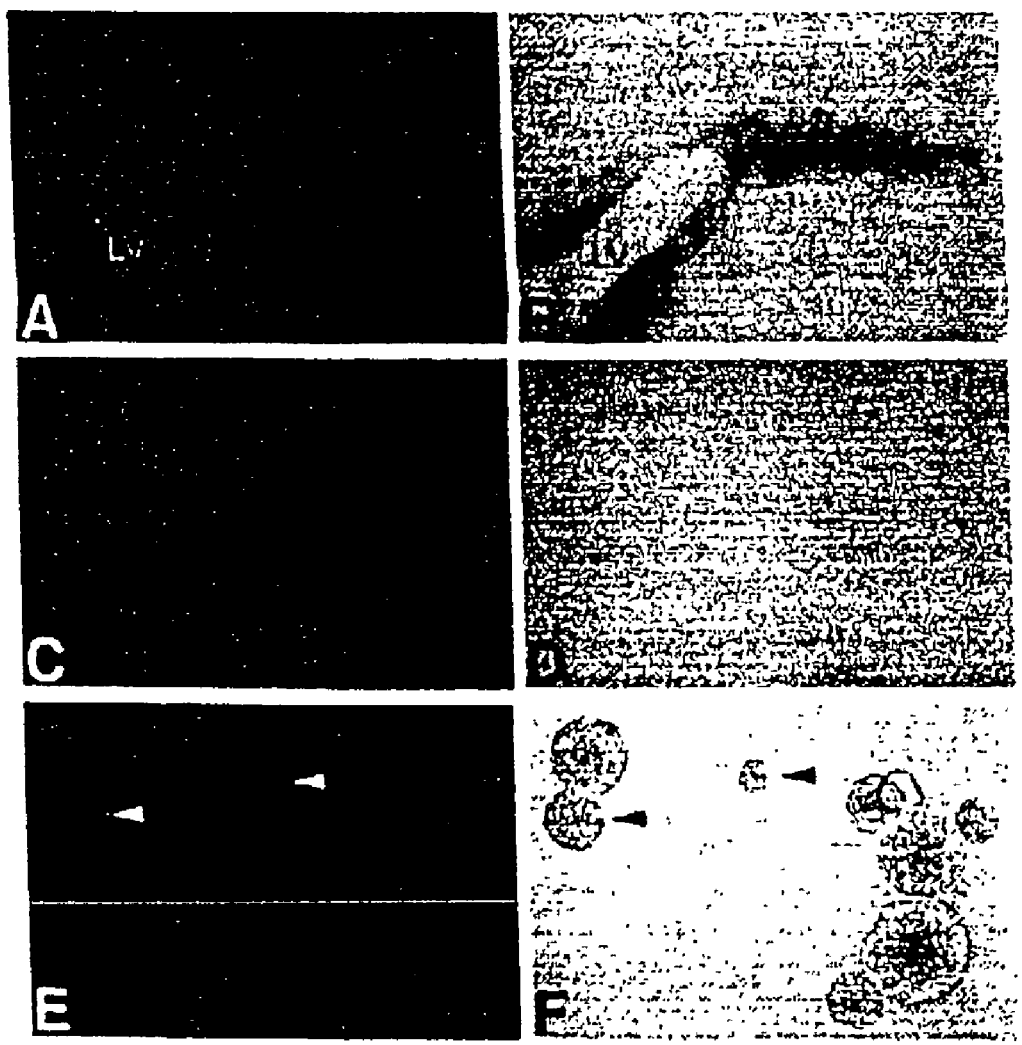
FIG. 2 illustrates the generation of olfactory bulb neurons and neurospheres.

FIG. 2: Generation of Olfactory Bulb Neurons and Neurospheres

Ten days after injection of DiI (A, C) or replication-deficient adenovirus expressing LacZ (B, D) into the contralateral lateral ventricle, labelled cells are seen in the subventricular zone (A, B) and olfactory bulb (C, D). The inset in (C) shows DiI in a βIII-tubulin-inununoreactive neuron. Bright-field (E) and fluorescence (F) micrographs showing neurospheres from the brain of an animal which had received an intraventricular DiI injection. Two very weakly labelled or unlabeled neurospheres are indicated with arrowheads.

Figure 3:
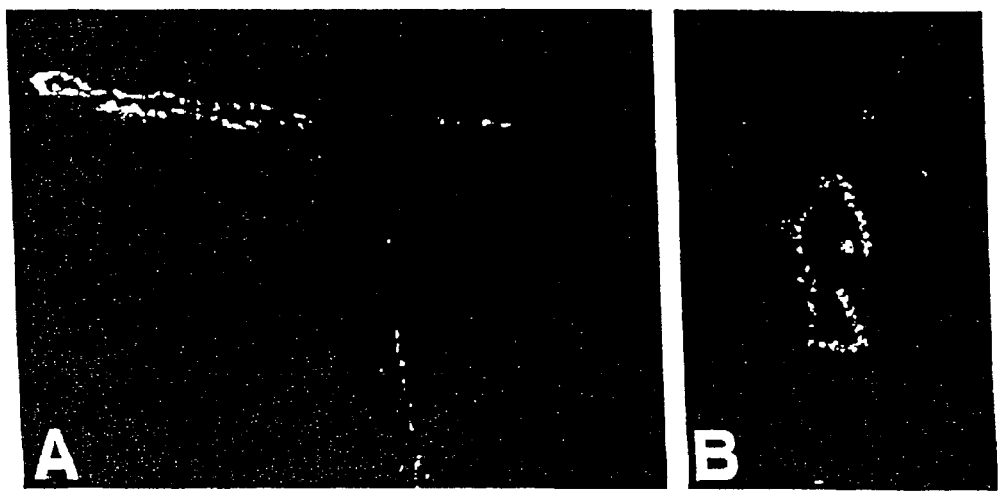
FIG. 3 illustrates the enrichment of neural stem cells with an ependymal cell specific marker.
Figure 3:
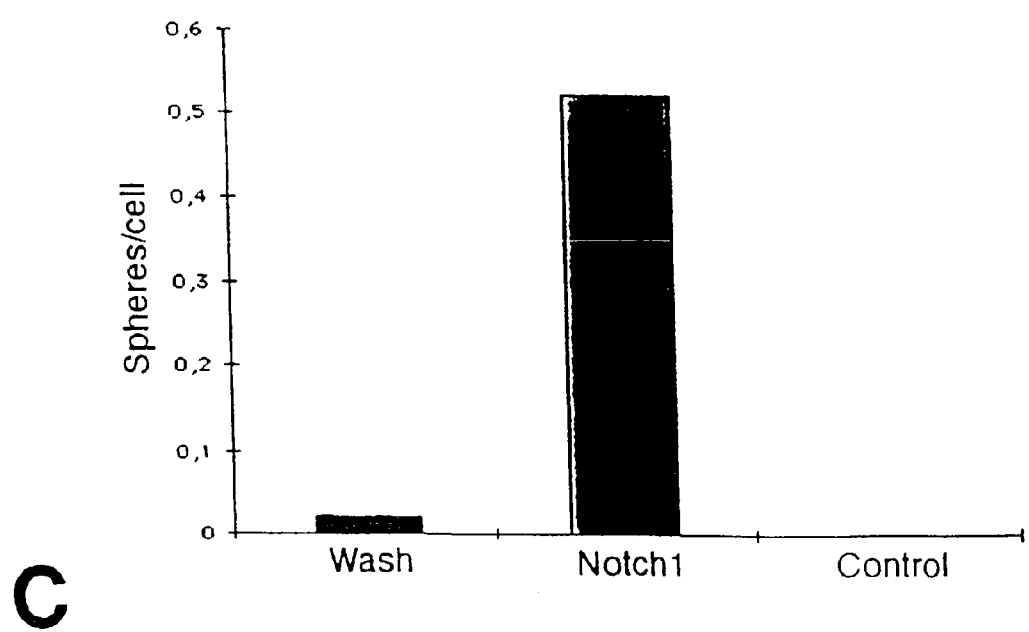

FIG. 3: Enrichment of Neural Stem Cells With an Ependymal Cell Specific Marker

Immunofluorescence localisation of Notch1 in the wall of the lateral ventricle (A) and in the spinal cord (B). Notch1 immunoreactivity is restricted to ependymal cells lining the lateral ventricle and central canal. The selective localisation of Notch1 to ependymal cells enabled enrichment of ependymal cells from acutely dissociated brain and spinal cord tissue. The dissociated cells were incubated with antisenim raised against Notch1, followed by incubation with magnetic bead conjugated secondary antibodies and magnetic separation of labelled (Notch1 fraction) and unlabeled cells (wash fraction). In control experiments, the primary antiserum was omitted. The number of cells in each fraction was calculated and the number of neurospheres generated in the different cultures was counted (C).

Figure 4:
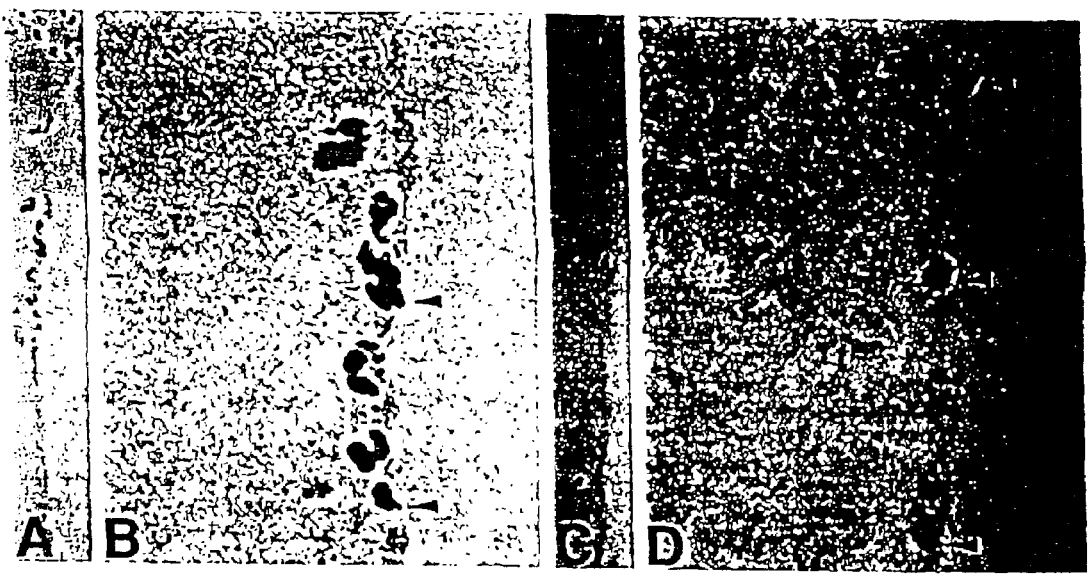
FIG. 4 illustrates the proliferation of ependymal cells by showing an immunohistochemical detection of 5-bromo-2'-deoxyuridine (BrdU) in the lateral wall of the lateral ventricle after two weeks continuous BrdU administration (A,B) or two weeks administration followed by one week without BrdU (C,D).

FIG. 4: Proliferation of Ependymal Cells

Immunohistochemical detection of BrdU in the lateral wall of the lateral ventricle after two weeks continuous BrdU administration (A, B) or two weeks administration followed by one week without BrdU (C, D). (B) and (D) show details from (A) and (C), respectively. Labelled ependymal cells are indicated with arrowheads in (B) and (D).

Figure 5:
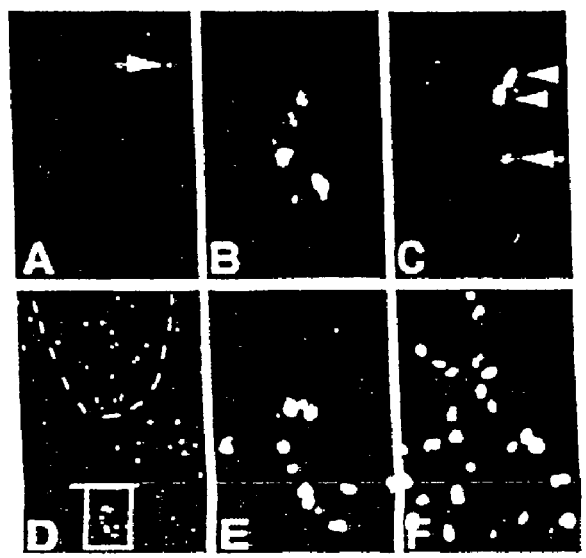
FIG. 5 discloses how the ependymal cell proliferation is induced by injury.
Figure 5:
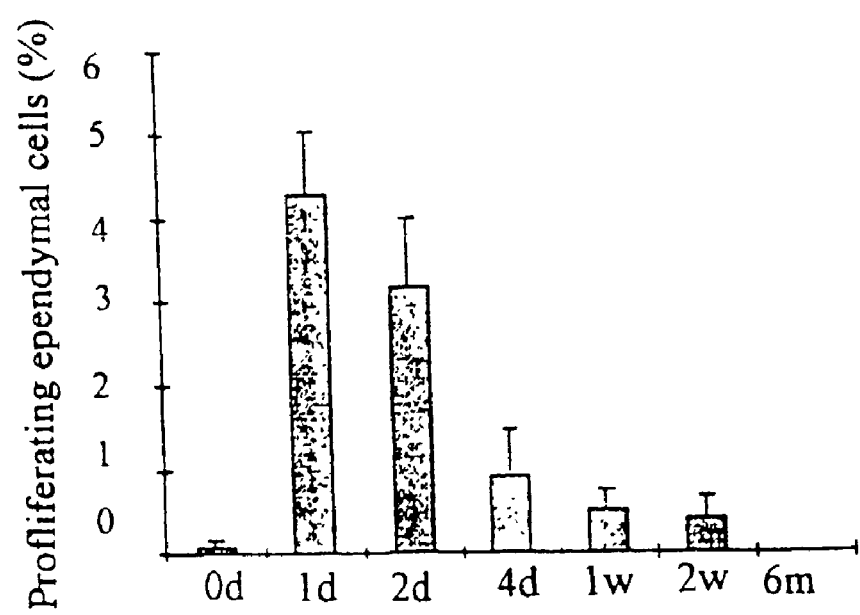

FIG. 5: Ependymal Cell Proliferation is Induced by Injury

Immunohistochemical detection of BrdU in the spinal cord after 8 hours (A, D-F) or two weeks administration (B, C) of BrdU. (G) Proportion of spinal cord ependymal cells incorporating BrdU administered during the last 8 hours before sacrifice (BrdU labelled nuclei/total number of ependymal cell nuclei visualised with propidium iodide, n=3-5 rats at each time point, error bars show SEM).

Figure 6:
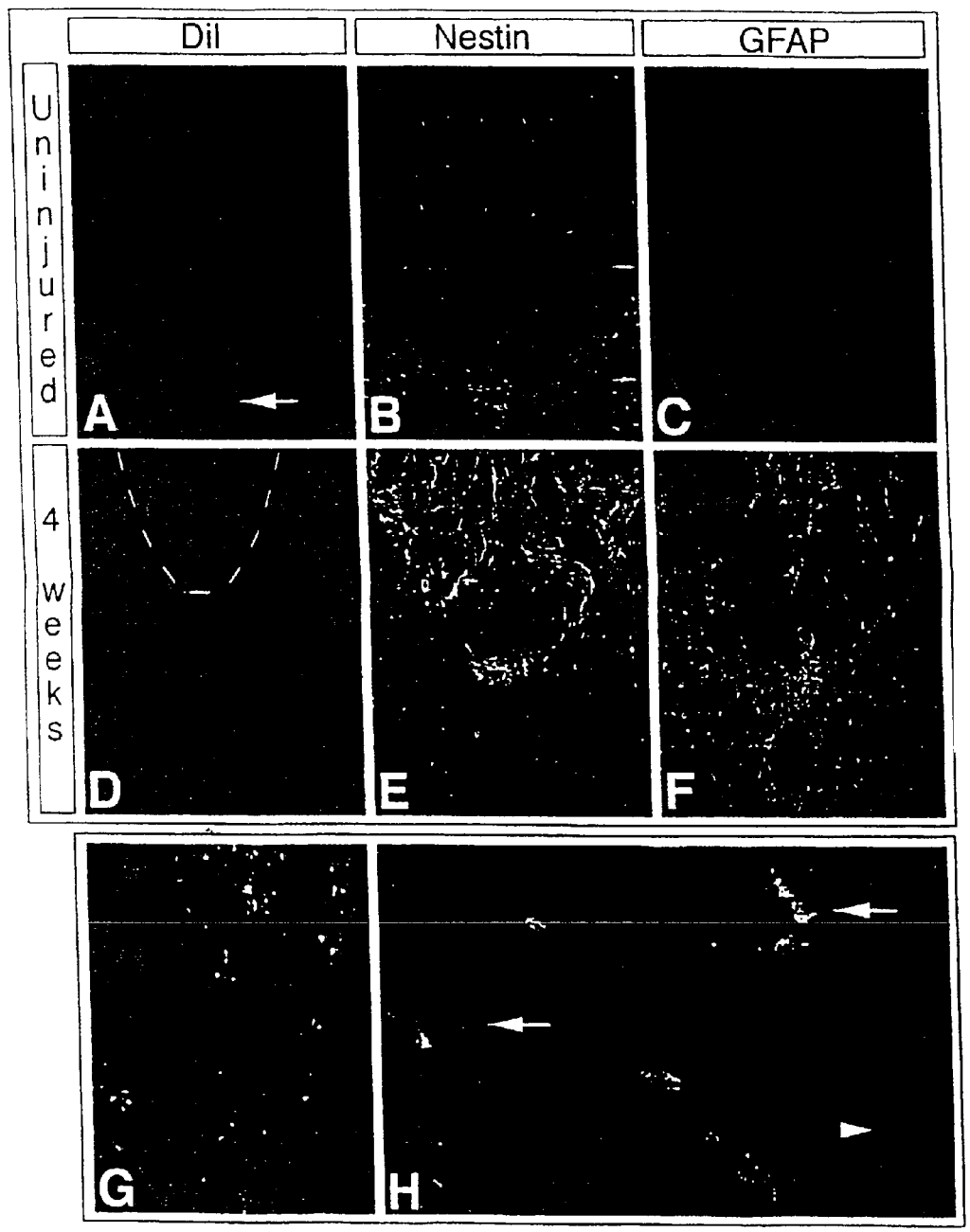
FIG. 6 shows the generation of astrocytes from ependymal cells after spinal cord injury.

FIG. 6: Generation of Astrocytes from Ependymal Cells after Spinal Cord Injury

Distribution of DiI, nestin- and GFAP-immunoreactivity in the spinal cord. The animal in (D-F) was subjected to a dorsal funiculus incision 4 weeks prior to analysis. All animals received an intraventricular DiI injection prior to injury. DiI and nestin-immunoreactivity immunoreactivity is shown in the same sections, and GFAP-immunoreactivity in an adjacent section in (A-F). The approximate delineation of the injured area is indicated by the broken line in (D). (G) shows DiI (red) and GFAP-immunoreactivity (green) in the dorsal funiculus 2 weeks after the lesion. A yellow signal indicates co-localisation of DiI and GFAP-immunoreactivity. (H) Confocal laser scanning microscope visualisation of DiI and GFAP-immunoreactivity in the scar tissue 2 weeks after injury. Two GFAP-immunoreactive DiI labelled cells are indicated by arrowheads, and a DiI labelled cell which does not show any detectable GFAP is indicated with an arrow.

Figure 7:
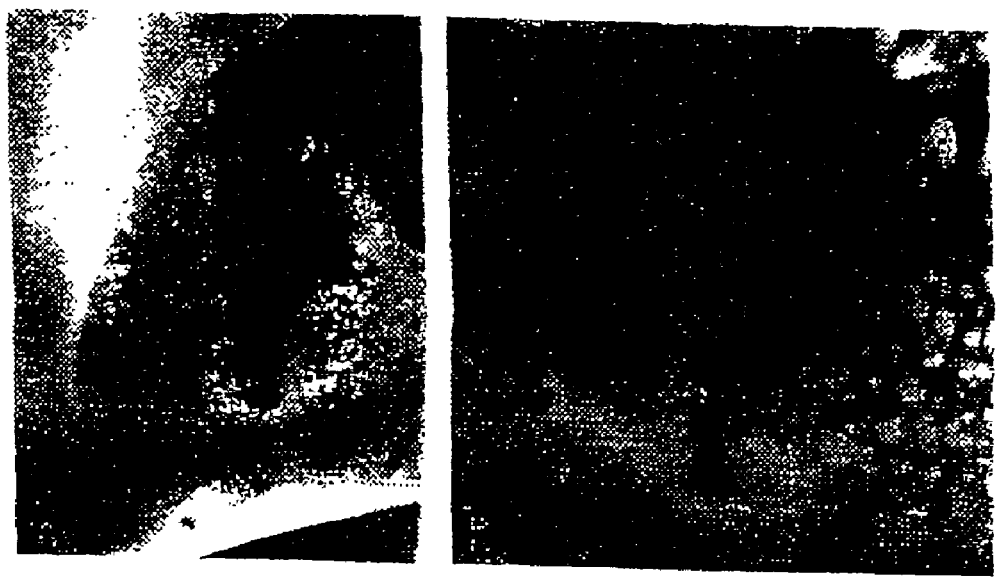
FIG. 7 discloses transplantation of purified of stem cells derived from transgenic animals.

FIG. 7 Transplantation of Neural Stem Cells

Transplantation of purified stem cells derived from transgenic mice expressing LacZ to the striatum of adult rats. The arrows point to a group of grafted cells. (B) shows a detail from (A).

FIG. 8

Generation of neurons in substantial nigra from stem cells in the ependymal layer in the adult rat. Microphotograph of nigral tyrosine hydroxylase-positive neurons (green) in substantial nigra pars compact also labelled with DiI (red) in rodents after administration of this fluorescent dye to the adult animal four months earlier. Arrows point at two nigral dopamine neurons containing the fluorescent marker labelling ependymal, neural stem cells.

FIG. 9

Migratory streams of stem cells from the ependymal layer or their progeny in the mouse midbrain. Arrows point at the ventromedial migratory streams (red cells) of the DiI 30 labelled ependymal cells that reach the medial substantial nigra pars compact (*). SNR=substantial nigra pars reticulata, IP=Interpeduncular nucleus. Arrows show lateral (I) and ventral (v) directions. Several pathways reaching rostral, caudal, medial and lateral parts of substantia nigra pars compacta respectively were identified. In addition to the illustrated ventromedial stream, a dorsolateral and a midline stream were identified.

FIG. 10

Generation of neurons in mouse hippocampus from stem cells localised in the ependymal layer. Microphotograph illustrating that the DiI labelled ependymal cells or their progeny migrate to the granule cell layer of the dentate gyrus (DG) of hippocampus. Arrows show lateral (I) and ventral (v) directions.

FIG. 11

In (A) one wild type embryonic day 11 embryo is shown (left) and a chimeric embryo generated from a blastocyst which was injected with brain neural stem cells from adult Rosa26 mice (right). There is some endogenous X-gal labelling in association with the otic vesicle in the wild type embryo. Contribution of cells from the adult neural stem cells is obvious in several tissues including for example heart and CNS in the injected embryo. In (B) lacZ cDNA from amnion (A), head region (H), thoracic (Th) or caudal region (C) was amplified by RT-PCR. lacZ mRNA expression indicating chimerism is seen in the 3 injected embryos but not in the control. Primers to L19 were used as internal control.

FIG. 12

Immunohistochemical detection of b-galactosidase (A, B) and desmin (C, D) in a section through the thoracic cavity of an embryonic day 11 embryo. In (E) and (F) b-galactosidase (green) and desmin immunolabelling (red) are shown together demonstrating co-localisation in the heart.

Figure 13:
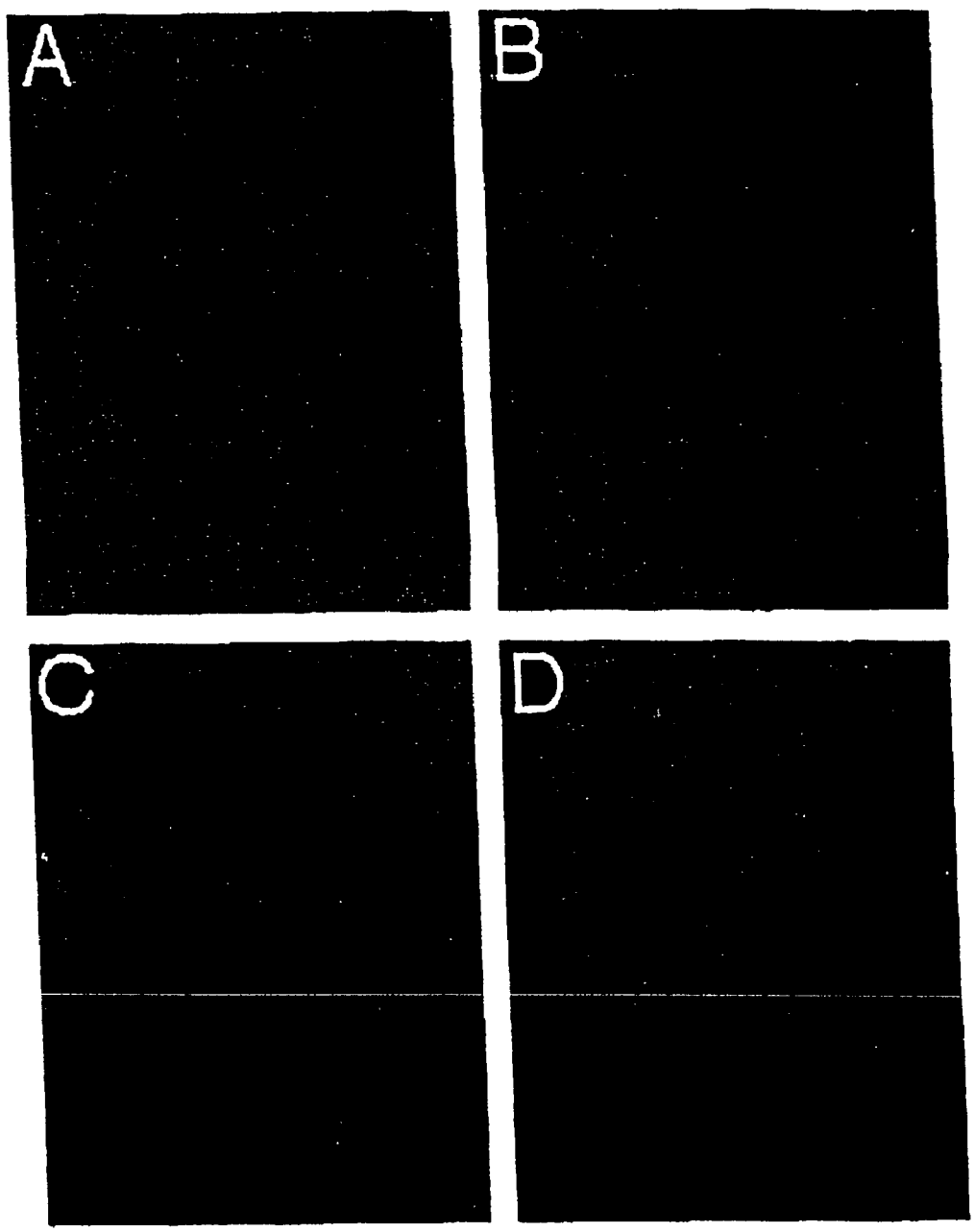
FIG. 13 presents abdominal contribution of adult neural ependymal stem cells to specialised tissues.

FIG. 13 immunolabelling for b-galactosidase (A) and desmin (B) in a section through the upper abdominal cavity of an 11 day old embryo. The liver shows strong b-galactosidase expression (A). In (C) the b-galactosidase and desmin immunostaining are shown together demonstrating co-localisation in the apex of the heart. (D) shows b-galactosidase immunolabelling in the intestine.

EXAMPLES

1. Labelling of Ependymal Cells and their Progeny In Vivo

To test whether neurons may be generated from ependymal cells, we injected the fluorescent label DiI or a replication deficient adenovirus expressing the reporter-gene LacZ into the lateral ventricles of adult rats or mice. Male Sprague-Dawley rats weighing 280-320 g or male C57BL/6 mice weighing 25-30 g were anaesthetised with chloral hydrate (400 mg/kg). Unilateral stereotaxic injections of 10 μl (rats) or 3 μl (mice) of 0.2% w/v DiI (Molecular Probes) in DMSO or 50 μl adenovirus solution (containing $10^9$ plaque forming units) were made 0.9 mm (rats) or 0.5 mm (rnice) posterior and 1.4 mm (rats) or 0.7 mm (mice) lateral to Bregma and 4 mm (rats) or 2 mm (mice) below the dura mater into the lateral ventricle. The injections resulted in specific labelling of the ependymal layer throughout the ventricular system; no labelling was seen in the subventricular zone nor in the brain parenchyma (FIG. 1). Thus, this method makes it possible to specifically follow the fate of the labelled ependymal cells and their progeny. Analysis of the distribution of DiI revealed an increasing number of labelled cells in the rostral migratory stream (Goldman et al., Trends Neurosci. 21:108), and after 10 days the first DiI labelled neurons were seen in the olfactory bulb, a region where new neurons are added continuously in adult mammals (FIG. 2). Similarly, in animals injected with the adenovirus, LacZ expressing cells were found in the olfactory bulb from 10 days after the injection, albeit at much lower numbers than in the DiI injected animals as expected since the adenovirus is replication deficient and the label will thus only be inherited by a subset of the progeny of the infected cell (FIG. 2). LacZ expression was detected with X-gal staining as described (Park et al., EMBO J. 16:3106).

2. Identification and Localisation of Neural Stem Cells by Culturing Labelled Ependymal Cells The specific labelling of ependyma in vivo may be used to test whether the labelled cells have stem cell properties in vitro. After an injection of DiI (described above), rats were killed with $CO_2$, their brains removed and kept in ice-cold PBS. The lateral walls of the lateral ventricles were dissected out. The tissue was minced with scissors, shifted to 4 ml of dissociation medium (0.075% collagenase type 1 (Worthington), 0.075% hyaluronidase (Sigma), 2000U DNAse I in 4 ml 0.2M PIPES (Signa) and incubated at 37° C. for 30 min. Mechanical dissociation by gentle successive trituration through a 5 ml and 1 ml Pasteur pipette was followed by leaving the suspension for 2 min., allowing larger fragments to settle to the bottom. Then the supernatant was passed through a 40 μm mesh (Falcon). To the filtered suspension, 4 ml of cold medium (DMEM/F12) was added. Cells were spun down at 200 g for 4 min. The supernatant was removed, the pellet resuspended in 10 ml sucrose solution (0.9M in 0.5×HBSS) and centrifuged for 10 min. at 750 g. The supernatant was removed and the pellet resuspended in 2 ml of culture medium, placed on top of 10 ml 4% BSA in EBSS solution and centrifuged at 200 g for 7 min., followed by a washing step in DMEM/F12. The culture medium was made of: 0.5 ml L-glutamine, 0.75 ml 1M HEPES (15 mM), 50 μl 20 μg/ml EGF (and/or 50 μl 10 μg/ml bFGF), 1 ml B27 supplement, 0.5 ml 100×penicillin/streptomycin stock and, finally, DMEM-F12 medium to a total volume of 50 ml. Cell cultures were maintained at 37° C., 5% $CO_2$ in a humid atmosphere. Under these conditions, characteristic spheroid cell aggregates of undifferentiated cells were formed in the cultures. These cell aggregates derive from a single stem cell and thus represent a clone of cells. Of these spheres, 88.6±1.20% and 89.0±1.23% from lateral ventricle and spinal cord, respectively, were clearly DiI labelled (mean from 5 independent experiments±SEM). DiI labelled spheres were collected and dissociated to single cells. Many of these cells formed new spheres, and when induced to differentiate by adding serum to the medium, most of these secondary spheres generated neurons, astrocytes and oligodendrocytes. Generation of differentiated progeny was demonstrated by immunohistochemical labelling with the following cell type specific antibodies: anti-glial fibrillary acidic protein (Dako) for astrocytes, Tuj 1 (Babco) for neurons and 04 (Boehringer Mannheim) for oligodendrocytes. These experiments identify a useful method to study ependymal cells in vitro and demonstrate that ependymal cells have self-renewal capacity and that they are multipotent, i.e. they are bona fide stem cells.

3. Culture Protocol and Media

Culture protocols suitable for growing and screening ependymal neural stem cells can be found in Johansson et al, Cell 96:25. However, the most important ingredient in the tissue culture medium for the ependymal neural CNS stem cells is a mitogen which can 20 be either epidermal growth factor (EGF) or fibroblast growth factor (FGF). The second most important factor is to have an adequate supply of cofactors and nutrients, preferably the well-known supplements B27 or N2. The following special media were used:

| Medium for neurospheres: | |
| --- | --- |
| DMEM/F12 | 47 ml |
| B27 | 1 ml |
| L-glutamine (Stock: 200 mM) | 0.5 ml |
| Penicillin/Streptomycin (10000 U each) | 0.5 ml |
| HEPES (Stock: 1 M) | 0.75 ml |
| EGF-Receptor Grade (Stock: 20 μg/ml) | 0.05 ml and/or |
| BFGF (Stock: 10 μg/ml) | 0.05 ml |
| HBSS-Glucose solution | 500 ml |
| HBSS, 10X | 50 ml |
| D-glucose (Stock: 300 mg/ml) | 9.0 ml |
| HEPES (Stock: 1 M) | 7.5 ml |

-continued

Medium for neurospheres:

| | |
|---|---|
| ddH$_2$O | 433.5 ml |
| **pH to 7.5 | |
| Sucrose-HBSS solution | 500 ml |
| HBSS, 10X | 25 ml |
| Sucrose | 154 g |
| ddH$_2$O | balance to 500 ml |
| **pH to 7.5 | |
| BSA-EBSS-HEPES solution | 500 ml |
| BSA (Sigma catalogue no A4503) | 20 g |
| HEPES (Stock: 1 M) | 10 ml |
| EBSS, 1X | balance to 500 ml |
| **pH to 7.5 | |

4. Dissociation of Tissue 13.3 mg trypsin (Sigma catalogue no. T4665), 7.0 mg hyaluronidase (Sigma catalogue no. H3884) and 2.0 mg kynurenic acid (Sigma catalogue no. K3375) were dissolved together in HBSS-glucose solution at 37° C. The solution was filter-sterilised and then, 200 µl 4000 U/ml DNAse (Sigma catalogue no. D4527) was added. Ependyrnal tissue was dissociated in this medium at 37° C. for 15 minutes. The reaction was triturated gently 10 times with a 5 ml pipette, and then the incubation was continued for an additional 15 minutes. Incubation in this medium should not be longer than 30 minutes.

Immediately afterwards, the dissociated tissue was passed through a 70 µm nylon cell strainer (Falcon no. 2350). The mixture was centrifuged at 1500 rpm for 5 minutes in a 15 ml conical tube, the supernatant was removed, and the pellet was resuspended in 10 ml sucrose-HBSS solution. The resuspended pellet was centrifuged at 2000 rpm for 10 minutes, the supernatant was removed, and the pellet was resuspended in 2 ml 1 X EBSS. A new 15 ml conical tube was filled with 12 ml of the BSA-EBSS-HEPES solution. The 2 ml cell suspension was carefully applied to the top and the resulting mixture was centrifuged for 7 minutes at 1500 rpm, the supernatant was removed, and the cells were resuspended in Neurosphere Medium and plated into 10 cm dishes.

The above procedure is ideal for the spinal cord since it removes most of the myelin. However, with small amounts of tissue and for cells isolated from the ventricular walls, the use of eppendorf tubes after the suspension in sucrose is more suitable and will result in more cells. Typically, the pellet was suspended in 4 ml of sucrose-HBSS solution, and this amount was divided into four 1.5 ml tubes. The volume of the BSA-EBSS-HEPES solution was scaled down accordingly.

5. Passage of Neurospheres

Trypsin (Life Technologies #45300027) is incubated for 24 hours at 37° C. The Trypsin is then diluted (if necessary) with PBS (Phosphate-Buffered Saline) to a level that will yield complete dissociation of neurospheres within 5 minutes (empirically determined for every 500 ml treated).

Neurospheres are collected from 10 cm plates and allowed to gently settle in a 15 ml conical tube. Once the spheres have been collected at the bottom tip, the supernatant is removed. The neurospheres are then suspended in 1×PBS, transferred to a 1 ml eppendorf tube, and allowed to settle. The supernatant is removed, and 500 µl Trypsin (37° C.) is added to the spheres. After 2 minutes incubation at 37° C., the spheres are gently triturated through a yellow 200 µl pipette tip and then left for three additional minutes. The spheres are again triturated, and any remaining clumps or spheres are allowed to settle for approximately 30 seconds. The upper 400-450 µl of trypsinised cells is removed and placed in a new eppendorf tube containing an equal volume of BSA-EBSS-HEPES solution. The cells are then centrifuged at 1500 rpm for 1 minute, the cell pellet is resuspended in 1×PBS and then it is centrifuged again at 1500 rpm for 1 minute. The supernatant is then removed and the cell pellet resuspended in 50:50 Neurosphere Medium:Conditioned Medium (Conditioned Medium is collected from neurosphere cultures that have been in culture for at least one week. Medium is removed from the cultures, filtered through a 0.2 µm filter, and then mixed with an equal volume of freshly made Neurosphere Medium.). The cells are then plated in the same medium but on bacterial plates (not Tissue Culture-treated plates) or a large proportion of the cells will initially adhere to the bottom of the plate which will inhibit the formation of new spheres. After 24 hours, the cells can be replaced onto tissue culture plates, if desired.

6. Culture of Single Ependymal Neural Stem Cells

A direct test of the potential of ependymal cells to form neurospheres would be to culture individual ependymal cells in vitro (Johansson et al. Cell 96:25) To this end, we isolated ependymal cells from dissociated lateral ventricle wall tissue by two criteria. First, the cells had to possess cilia, a distinct morphological characteristic of ependymal cells, but not for cells from the subventricular zone. Second, the tissue was taken from animals which had received a DiI injection 6 hours before sacrifice, and only DiI labelled cells were collected. Cells that fulfilled both criteria were picked and transferred to microwells. One cell was cultured per well in neurosphere conditioned medium. In these cultures, 58% (111 out of 192 cells) of the ependymal cells underwent cell division. In the majority of these wells (99 wells), the cells died within a few days or formed very small cell clusters. However, 6.2% of the initial cells (12 out of 192) formed large neurospheres. When serum was added to the medium of these neurospheres, cells expressing cell type specific markers for neurons, astrocytes and oligodendrocytes were identified. This revealed that single ependymal cells are capable of forming neurospheres that can generate neurons, astrocytes and oligodendrocytes, i.e. they are bona fide neural stem cells.

7. Validation of the DiI Labelling Method

As some results critically depend on the unique DiI labelling of ependymal cells, but not of cells in the subventricular zone, the possibility of DiI transfer to the subventricular cells had to be ruled out. To exclude direct cell to cell transfer of DiI from the ependymal cells we co-cultured DiI labelled ependymal cells with genetically labelled cells from ROSA 26 mice. No detectable transfer of DiI to the ROSA 26 cells could be observed. To rule out the possibility of passive DiI diffusion from the cerebrospinal fluid to subventricular cells over time, we aspirated cerebrospinal fluid from the lateral ventricle from animals which had received an intraventricular DiI injection the day before and added it to cultured cells. We found only weak labelling, indicating that the DiI concentration was very low. Moreover, injection of the cerebrospinal fluid into the lateral ventricle of another animal, did not result in any labelling of cells lining the ventricle. These data suggest that the DiI concentration in the lateral ventricle drops fast after an intraventricular injection and that a delayed passive labelling of cells in the subventricular zone is very unlikely.

8. Purification of Neural Stem Cells by Cell Sorting

We have found that Notch1 protein, a cell surface receptor expressed in the nervous system during embryonic development (Kopan et al., Trends Genet. 13:465), is selectively expressed in ependymal cells but not in subventricular zone cells in the adult rat brain and spinal cord (FIG. 3). We took advantage of this selective expression of Notch1 to isolate ependymal cells from acutely dissociated lateral ventricle wall and spinal cord tissue by magnetic sorting with Notch1 antiserum. For magnetic sorting, cells were collected as above and resuspended in 100 μl culture medium of the above defined composition, 1 μl of rabbit antiserum raised against Notch1 was added and incubated at 4° C. for 20 min. Subsequently, cells were washed with 6 ml of DMEM/F12, the pellet was resuspended in 100 μl of culture medium and 30 μl of pre-washed (with 0.5% BSA in PBS) magnetic bead-conjugated anti-rabbit antiserum ($1.8-2.1 \times 10^7$ beads, Dynal) was added and incubated for 20 min. at 4° C. with occasional shaking. After incubation, 2 ml of culture medium was added, the suspension transferred into a 2 ml Eppendorf tube, placed in a Dynal magnetic separator and left for 2 min. The supernatant was collected in a 35 mm uncoated Nunc dish ('wash' fraction), then the magnet was removed from the separator, 2 ml culture medium (as defined above) was added to resuspend the bead-cell suspension and the magnetic separation step was repeated. The supernatant was again transferred to a culture plate. After removal of the magnet, 2 ml of culture medium were added, the remaining cells resuspended and transferred to a 35 mm uncoated Nunc dish. Throughout the whole procedure, all solutions and the cell suspensions were kept cold. Cell cultures were maintained at 37° C., 5% $CO_2$ in a humid atmosphere. Culture medium (composition as described above) was renewed every 3-4 days. Cells which had magnetic beads attached (sorted) or not (wash fraction) were then cultured and assayed for the presence of stem cells. Neurospheres started to appear around day 4-5 after isolation. In experiments where the cells had been sorted with the Notch1 antiserum, but not in experiments where the Notch1 antiserum was omitted, the majority of spheres formed in the sorted fraction (FIG. 3). When spheres formed in the Notch1 sorted fraction were dissociated they formed secondary spheres which were multipotent corroborating that ependymal cells are neural stem cells. In other experiments, in vivo labelling of ependymal cells (see above) with DiI was followed by fluorescence activated cell sorting (FACS) or manual picking of fluorescent cells and resulted in highly enriched cultures of ependymal cells.

9. Ependymal Cells have a Slow Proliferation Rate and Generate a Transit Amplifying Precursor Population Previous studies, based on the lack of incorporation of labelled nucleotides after a single or a few injections, have indicated that ependymal cells do not proliferate in adult mammals. A characteristic feature of stem cells is that they proliferate slowly or rarely and administration of labelled nucleotides over long time periods have been used to identify slowly cycling stem cells in other tissues. It is thus likely that a slow proliferation rate of ependyrnal cells, which one would expect if they were stem cells, would be missed if analysed by a single or a few injections of labelled nucleotides. In order to characterise the proliferation of ependymal cells, we supplied the thymidine analogue 5-bromo-2'-deoxyuridine (BrdU, Sigma) continuously over long time periods. Rather than doing repeated injections, we administered BrdU to adult mice through the drinking water over a two to six week period before analysis. To achieve long term labelling of the mouse brain, we added 1 mg/ml BrdU to the drinking water of mice. The water was exchanged twice a week and protected from light with aluminium foil. BrdU was efficiently taken up through the intestine, and resulted in labelling of ependymal cells lining the lateral walls of the lateral ventricles. Ependymal cells lining the roof and the medial wall of the lateral ventricles were rarely labelled, corresponding to the lateral wall being the most active neurogenic region. Very large numbers of BrdU labelled cells were present in the subventricular zone (FIG. 4). The labelled cells in the subventricular zone were often grouped in tight cell clusters, giving the impression of being a clone of cells (FIG. 4). Strikingly, in many cases such a cell cluster was located in close proximity to a labelled ependymal cell (FIG. 4). The proliferating precursor cells migrate closely together in the subventricular zone to the antero-lateral tip of the lateral ventricle where they enter the rostral migratory stream. The spatial relationship between a labelled ependymal cell and a cluster of subventricular zone cells was in the vast majority of cases so that the subependyrnal cells were shifted toward the rostral migratory stream in relation to the labelled ependymal cell (FIG. 4).

The fact that stem cells have a low proliferation rate has been used to localise stem cells in other tissues. When labelled nucleotides are administered over prolonged time periods, both rapidly and slowly proliferating cells will be labelled. By letting the animals survive for a period after the administration of the labelled nucleotide, rapidly proliferating cells will be given time to dilute the label by continued divisions or by migrating away. Therefore, only slowly proliferating cells will retain the label with time. We analysed animals which had received BrdU continuously over a two to six week period followed by 2 weeks without BrdU. In these animals, very few labelled cells were seen in the subventricular zone, indicating that the vast majority of cells had diluted the label by repeated divisions or migrated away (FIG. 4). However, a substantial number of ependymal cells were still labelled (FIG. 4 ).

We next studied the proliferation of spinal cord ependymal cells. A substantial number of ependymal cells lining the central canal were labelled after prolonged administration of BrdU through the drinking water (FIG. 5). In contrast to the lateral ventricle subventricular zone, a few labelled cells were seen just outside the central canal ependyma (FIG. 5). However, the few labelled cells that were seen close to the central canal often resided in close proximity with a labelled ependymal cell, suggesting that this cell may derive from the ependyma (FIG. 5).

10. Culture of Ependymal Neural CNS Stem Cells from the Adult Human Brain

Lateral ventricle wall tissue was removed from two adult patients during surgery to remove epileptic foci. The tissue was dissociated enzymatically as describe in detail for the rodent tissue, processed and cultured in the exact same way. After approximately one week, typical neurospheres appeared in the culture dishes. When induced to differentiate by plating the neurospheres on poly-L-ornithine or by adding serum, neurons, astrocytes and oligodendrocytes (studied with the same cell specific markers as in the rodent experiments) differentiated from single neurospheres.

11. A Quantitative Method Analysing Neurogenesis in Vivo in a Defined Brain Region Such as Substantia Nigra Pars Compacia in the Midbrain Several unpublished data from the present inventors have prompted them to postulate that the region of the brain where dopamine neurons die in Parkinson's disease, i.e. substantia nigra (Date, Brain Res. Bull. 40:1) represents a new region where a continuous turnover of neurons is present. 'State of the art' stereological cell counting techniques in situ have been utilised and further developed (Gundersen et al., APMIS 96:857; Janson et al., Neuroscience 57:931) and the total number of nigral neurons in young and aged mice, as well as the total number of apoptotic neurons in the same region, analysed. Briefly, the present inventor's unpublished results (Janson et al.) indicate that young and aged mice have the same number of nigral dopamine neurons, although a low number of neurons die spontaneously through apoptosis. At the same time the present inventors have found that nestin, a marker for neuronal progenitor cells as described above, is present in a subpopulation of nigral neurons (unpublished data, Janson et al.). Taken together these data indicate the possibility of a continuous neurogenesis in balance with neuronal apoptosis, i.e. neuronal turnover, which is described below. The quantitative method allows in vivo screening of substances enhancing neurogenesis and/or neuronal migration.

Figure 8:
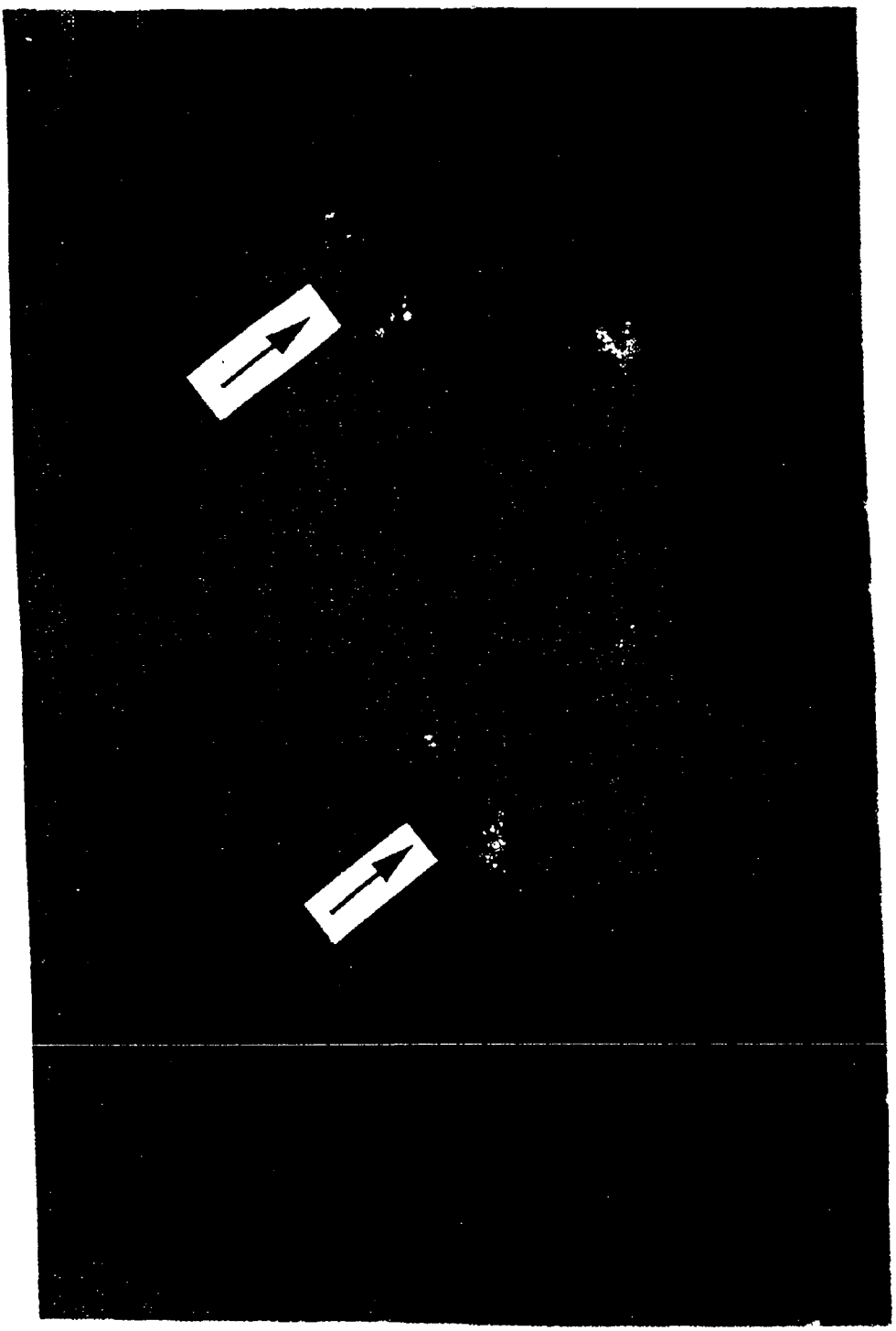
FIG. 8 shows the generation of neurons in substantial nigra from stem cells in the adult mouse.

Adult rats and mice were given DiI through intraventricular injections as described in the example above. At various time intervals after the injection (hours-months), the animals were transcardially perfused with 15 ml 0.9% saline, followed by 50 ml of +4° C. 4% (w/v) paraformaldehyde and 0.4% (v/v) picric acid in 0.1 M phosphate buffered saline, pH 6.9, during 5 min. After brain removal, the tissue was fixed for an additional 90 minutes in the same fixative and cryoprotected in buffered sucrose (10% for 24h, 30% for 2 days) at +4° C. The entire midbrain was cut with a cryostat using a systematic, uniform random sampling design, where 40 µm thick frontal sections were taken to six parallel rostrocaudal series. One series of sections was kept in 0.1 M PBS and the fluorescent signal was immediately converted to a permanent diaminobenzidine (DAB) signal using a modified previously described protocol (Singleton et al., J. Neurosci. Meth. 64:47). Thus, the sampled freshly cut free-floating sections were immersed for 10 min. in 1% $H_2O_2$ in 0.1 M Tris (pH 8.2) and then washed in buffer alone. Then the tissue was pre-incubated in the dark for 60 min. at +4° C. with filtered DAB (1.5 mg/ml of Tris buffer pH 8.2), rinsed in Tris buffer and then mounted on a glass slide and covered with fresh DAB solution, which was replaced with fresh solution every 30 min. during the photoconversion process. On each sampled slide substantia nigra was identified and the section was irradiated with ultraviolet light utilising a 10× objective and a rhodamine filter in an epifluorescence microscope (Nikon). The photoconversion process was carefully evaluated and when all the fluorescent signal in substantia nigra was visualised with the brown DAB product, the sections were immunohistochemically labelled with a marker (Vector SG, Vector) for dopamine neurons (tyrosine hydroxylase) utilising the avidin-biotin-immunoperoxidase system (Vector) (Janson et al., Neuroscience 57:931). The five parallel series of sections were instead stored in 30% sucrose in 0.1 M PBS at −20° C. until they were processed for immunohistochemistry and analysed in a confocal laser scanning microscope utilising several markers for glia and neurons (with appropriate controls) to determine the neuronal phenotype of the DiI labelled cells in substantia nigra pars compacta (FIG. 8). Quantitative estimates of the total number of TH immunoreactive cell bodies counterstained with cresyl violet (TH/CV+neurons) as well as TH immunoreactive cell bodies also containing DiI label were made in the bilateral SNc. Neuronal counts were determined using coded sections and a stereological technique, the optical fractionator (Janson et al., Neuroscience 57:931). Briefly, the unbiasedly sampled sections in rostrocaudal order were analysed with a CAST-Grid system (Computer Assisted Stereological Toolbox, Olympus, Albertslund, Denmark), which consists of a video camera on an Olympus BH2 microscope with a motorised specimen stage and a microcator to monitor movements in the z-axis (Heidenhain, Traunreut, Germany); both are linked to a PC with GRID software and a high resolution monitor. After encircling the SNc area in each sampled section a low magnification, the analysis was performed at high magnification (100×oil immersion, numerical aperture 1.4). This allowed a clear visualisation of individual cells in the densely populated encircled area as the focus moved through the tissue, which was optically dissected into thin slices and assessed by the microcator with a resolution of 0.5 µm. A computerised, uniform, systematic random sampling of small volumes (extending 6-9 µm along the thickness of the section) was carried out; neurons with their nucleoli inside the sampling volume that fulfilled the stereological criteria were counted in a known fraction of the entire nigral volume. As described earlier (Chan et al., J. Pharmacol. Exp. Ther. 280:439), nigral neurons were counted if they showed both Nissl stained perikarya and TH immunoreactivity within the cell body and/or its dendrites. In the series of sections where the DiI signal was photoconverted, TH+neurons containing DiI were counted (evaluation at 3,600×). The coefficient of error for each estimate of the total number of labelled neurons in different categories was determined. The obtained counts are independent of any dimensional changes in the tissue during processing such as shrinkage, which was determined along the z-axis. The total number of nigral dopamine neurons at various time points (a few hours to 60 days) were plotted against time, and from the regression curve ($r^2$=0.97) 175 new neurons were found to be generated each week in this brain region, which is around one per cent of the total number of nigral dopamine neurons in the mouse.

Figure 9:
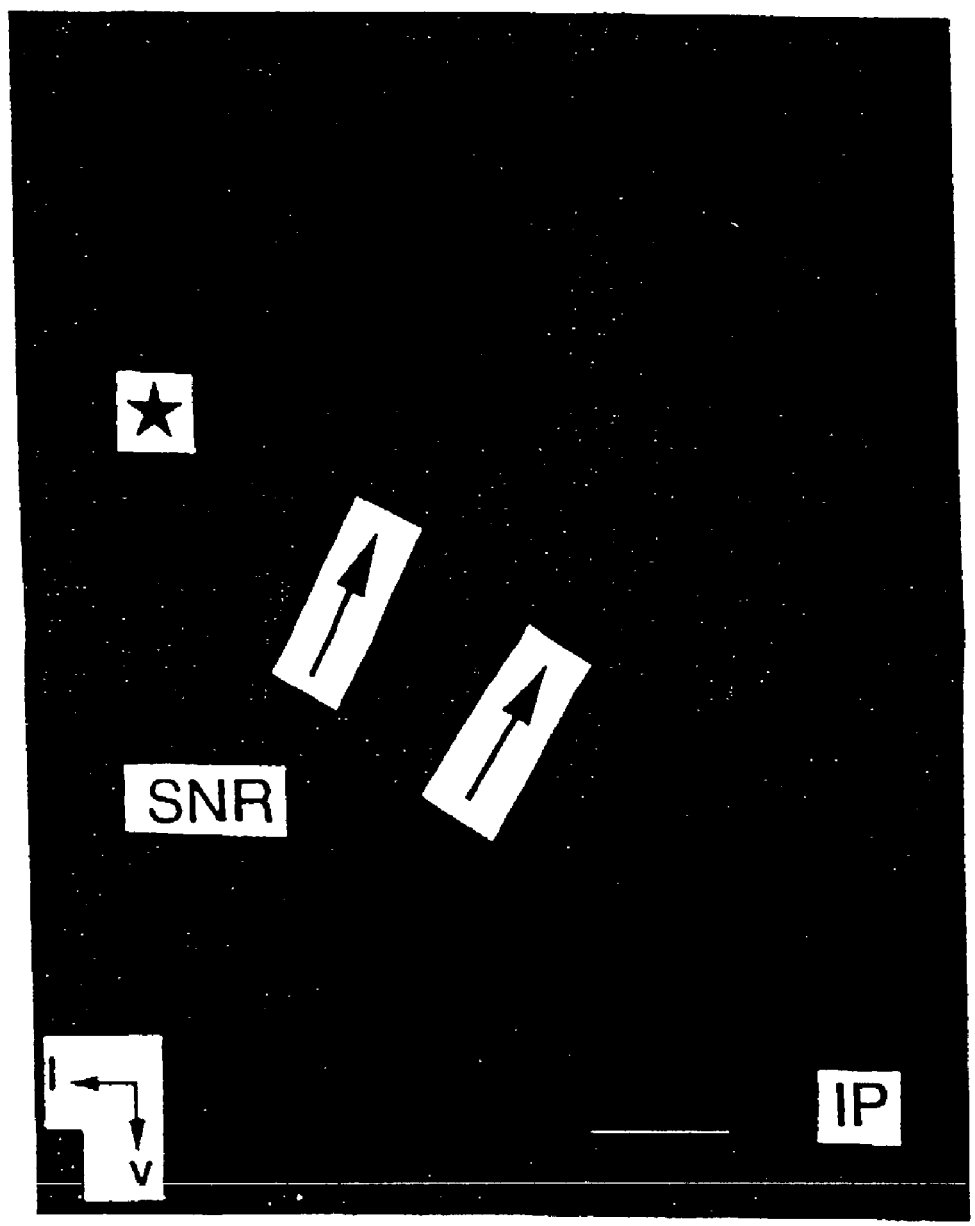
FIG. 9 illustrates migratory streams of stem cells or their progeny in the midbrain.

Several migratory streams of DiI labelled cells were characterised as they reached different parts of substantia nigra pars compacta (not known or described before, FIG. 9). With the application of a modified protocol for cell counting using a fluorescent microscope, the total number of cells in each of the defined migratory streams is being determined. The interpretation that the DiI labelled neurons were indeed newly generated was confirmed with BrdU labelling in animals receiving chronic administration via drinking water (1 mg/ml, see example above, or by repeated intrapentoneal injections of BrdU). Furthermore, evidence that the 'new' neurons were functional and developed appropriate neuronal processes for projection neurons was supported by the finding of DiI and/or BrdU in some of the TH+nigral neurons that also demonstrated a cell body label retrogradely transported from the nerve terminal region in the striatum (FluoroGold).

Figure 10:
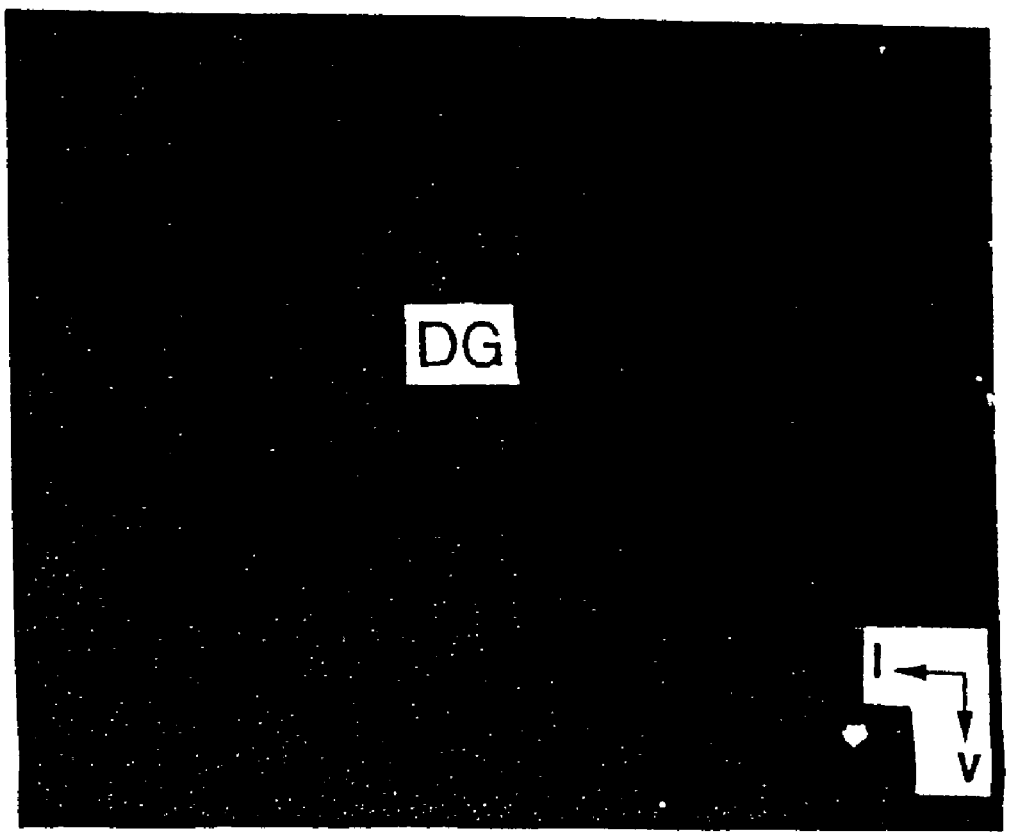
FIG. 10 discloses the generation of neurons in hippocampus from stem cells localised in the ependymal layer.

12. The Progeny of Labelled Ependymal Stem Cells Include Neurons in Several Brain Regions and of Various Phenotypes Utilising the in vivo fluorescent labelling protocol described above, we identified several regions of the brain where DiI labelled cells were identified as neurons. These regions include several parts of the hippocampus, including the granular layer of the dentate gyrus (FIG. 10), cortical layers and subcortical structures such as the presumably gamma-aminobutyric-acid (GABA)-containing neurons in the subthalamic and substantia nigra pars reticulata regions as well as serotoninergic neurons in the raphe brain nuclei and noradrenergic neurons in the locus coeruleus.

13. Generation of Genetically Modified Stem Cells in vitro

Genetically engineered stem cells were generated by culturing the stem cells as above, and then transfecting them with expression plasmids or viral vectors. For each transfection, 4 µg DNA (the method was established using the plasmid CMV-GFP from Clontech, encoding the green fluorescent protein (GFP) as a reporter) was added to 200 µl culture medium (defined above) in a 12×75 mm conical tube (15 ml) and gently rixed. In a second conical tube 15 µl Lipofectamine reagent was added into 200 µl culture medium and vortexed gently. The two solutions were then combined by adding the second to the first and incubated at room temperature 45 min. to allow DNA-liposome complexes to form. Then 1.6 ml culture medium was added to the tube with the DNA-liposome complexes and this solution was overlaid on the cells (which had the majority of their medium carefully removed). Cells were incubated 12 hours and then the medium was replaced with the regular culture medium without DNA. GFP detection was performed in a fluorescence microscope 48-72 hours post-transfection. These stem cells could be clonally expanded to generate spheres of undifferentiated genetically modified stem cells.

14. Altered Gene Expression in Stem Cells in Vivo

The feasibility of altering gene expression in stem cells in vivo was done by injecting a replication deficient adenovirus carrying the reporter-gene LacZ under the control of the RSV promoter into the lateral ventricles as described above. X-gal staining (described above) demonstrated expression of a reporter-gene in ependymal stem cells, and thus the feasibility of altering gene expression in stem cells. Stem cells carrying genes driving the expression of nerve growth factor, glial cell-line-derived neurotrophic factor (neuronal survival factor), bcl-2 (a gene which will promote the survival of the stem cells) and nurr1 (which may promote the generation of dopaminergic neurons from stem cells) are being generated.

15. The Use of Stem Cells from Transgenic Animals

We have found that it is possible to culture stem cells from transgenic animals. For these studies we have used mice carrying the LacZ gene in their genome (Zarnbrowicz et al. Proc. Natl. Acad. Scl. U S A., 94:3789). These mice express the transgene ubiquitously in all tissues (Zambrowicz et al. Proc. Natl. Acad. Sci. U S A., 94:3789). Stem cells from these mice were purified and cultured as above. Strong transgene expression was revealed by X-gal staining as described above.

16. Manipulation of Stem Cell Proliferation and Differentiation by Traumatic Injury In adult rats a laminectomy was performed at the mid thoracic level to expose the spinal cord, and the dorsal finiculus was cut transversely with microsurgical scissors, and the lesion was subsequently extended rostrally by a superficial longitudinal incision in the dorsal funiculus. In other animals, a hole was drilled in the skull and a needle was inserted into the brain tissue to induce an injury. In some animals the ependymal cells had been labelled 1-10 days before the injury by a DiI injection as described above. Quantification of the proportion of ependymal cells that proliferate at different time points after an incision in the dorsal furniculus revealed an almost 50-fold increase 1 day after the injury compared to uninjured animals (FIG. 5). After the first day, the proliferation gradually declined toward normal within one month (FIG. 5). Likewise, ependymal cell proliferation was greatly increased in the wall of the lateral ventricle following brain injury.

In animals in which the ependymal cells were labelled by a DiI injection prior to the spinal cord or brain injury, an increasing number of DiI labelled cells were seen progressively further outside the ependymal layer over the first four weeks after the injury (FIG. 6). DiI labelled cells were abundant in the forming scar tissue within one week after the lesion and persisted there for at least one year. Within the scar tissue forming at the injury the vast majority of the DiI-labelled cells showed immunoreactivity to glial fibrillary acidic protein, an astrocyte marker, indicating that the majority of progeny from ependymal cells had differentiated to astrocytes (FIG. 6). However, neuronal markers were not found in the DiI labelled cells indicating that the signals required for neuronal transformation of the stem cells were not present in this animal model.

17. Chemicals Increasing Neurogenesis in Substantia Nigra Pars Compacta in the Midbrain Separate mice were given 1-methyl-4-phenyl-1,2,3,6-tetrahydropyridine (MPTP, RBI, Natick, Mass., USA) (40 mg/kg diluted in physiological saline, sc.). This substance is known for its selective neurotoxic actions on dopamine neurons in the midbrain causing parkinsonism in humans and experimental animals (Langston et al., Science 219:979, Heikkila et al., Science 224:1451). However, the molecule also has structures in common with compounds known to act as neuroprotective agents in animal models of Parkinson's disease, e.g. nicotine (Janson et al., Neuroscience 57:931).

In our experiments animals were given MPTP or vehicle and the time course of changes in the number of DiI+nigral dopamine cells or in the staining pattern of the migratory streams of DiI+cells moving towards this brain region were analysed (see above, quantitative method to study neurogenesis in substantia nigra pars compacta in the midbrain after labelling of ependymal cells). The treatment led to higher numbers of TH+/DiI+as well as TH+/BrdU+nigral neurons indicating an increased neurogenesis. Also, the migratory streams of DiI+cells in the midbrain appeared more pronounced in animals treated with MPTP, which can be analysed quantitatively using the modified stereological method described above.

18. Transplantation of Ependymal Stem Cells

Ependymal stem cells from the brain or spinal cord of Rosa26 transgenic mice were purified and cultured as above. Spheres of undifferentiated stem cells from these mice were transplanted to the striatum of adult rats, by stereotaxic injection of spheres in 15 µl of their culture medium (described above). The animals were sacrificed 2 days later and the brains sectioned and analysed for the presence of LacZ expressing cells deriving from the Rosa26 mice by X-gal staining as described above. The grafted cells were scattered in the tissue close to the insertion canal. These cells often had several processes (FIG. 7).

19. Development of Assays for High Throughput Screening of Substances Influencing Neural Stem Cell Differentiation Test systems to efficiently assay the ability of substances to promote the differentiation of ependymal neural stem cells into a particular glial or neuronal phenotype are developed. Such substances could then be tested in vivo as outlined above.

20. Broad Potential of Adult Brain Neural Stem Cells to Generate Tissues of All Germ Layers

20 a. NSC Culture

The lateral wall of the lateral ventricles were enzymatically dissociated as described above (Johansson et. al., Cell,96:25). The culture medium consisted of 20 ng/ml EGF (Collaborative Biomedical Products), B27 supplement (Life Technologies), 2 mM glutamine, 100 U/ml penicillin, and 100 ug/ml streptomycin in DMEM-F12 medium (Life Technologies). EGF (20 ng/ml) was added to the medium every 48 hours after the initial plating of the cells.

20 b. RNA Analysis

Tissue RNAs were extracted using RNeasy (Qiagen), and 500 ng of total RNA was reverse transcribed into cDNA using Superscript II (Life Technologies) and random hexamers (Pharmacia) in a reaction volume of 50 µl. under conditions recommended by the manufacturer. PCR reactions were carried out in the presence of 2.5 mM $MgCl_2$, 10 mM Tris-HCl (pH 8.8 at 25° C.), 50 mM KCl, 0.08% Nonidet P40, 0.2 mM each dNTP, 5 U Taq DNA polymerase (Fermentas), 0.1 mg/ml BSA, 50 pmoles each oligonucleotide primer and in the presence of alpha [$^{32}P$] dCTP. To normalise the cDNA yields, a semiquantitative PCR reaction was performed using primers specific for cDNA encoding β-galactosidase in combination with primers specific for the ribosomal protein L19. Forty cycles of 94° C. (1 minute), 64° C. (1 minute), and 72° C. (1 minute) were used to amplify β-Galactosidase with the following oligonucleotide primer pair: sense oligonucleotide 5'-TTG GAG TGA CGG CAG TTA TCT GGA-3'(SEQ.ID.NO. 1) and antisense oligonucleotide 5'-TCA ACC ACC GCA CGA TAG AGA TTC-3'(SEQ.ID.NO. 2). After 25 cycles, the polymerase and oligonucleotide primers specific for L19 were added as an internal control: sense oligonucleotide 5'-CCT TGG ACA GAG TCT TGA TGA TCT CCT-3'(SEQ.ID.NO. 3) and antisense oligonucleotide 5"-CTT CTC AGG AGA TAC CGG GAA TCT AAG-3'(SEQ.ID.NO.4).

20 c. Immunohistochemistry

Cryostat sections and cultured cells were incubated with primary antibodies 1 hr at 37° C. or overnight at 4° C., rinsed in PBS, and incubated with secondary antiserum for 45 min. at room temperature.

20 d. Morulae Aggregation and Blastocyst Injection

Proliferating spheres of cells were trypsinised within four to 6 days after their initial isolation and resuspended in 1×PBS for aggregation or microinjection. Neural stem cells were either aggregated with CD-1 morulae or injected into blastocysts derived from C57BL mice and implanted into foster mothers using standard techniques and procedures.

20 e. Integration of Neural Stem Cells in the Inner Cell Mass of the Blastocyst In order to analyse the differentiative potential of adult neural stem cells, we assayed the ability of these cells to contribute to the formation of different tissues by introducing adult neural stem cells in the early embryonic environment and follow the fate of their progeny.

Multipotent neural stem cells can be propagated from dissociated adult brain and spinal cord tissue under certain culture conditions. Under these conditions, single cells proliferate and the progeny forms a cluster of aggregated cells. Such cell clones detach from the culture dish after a few days in vitro. In the presence of mitogens such as epidermal growth factor (EGF) or fibroblast growth factor (FGF), the cells continue to proliferate and form a characteristic spheroid cell aggregate, referred to as a neurosphere, of tightly clustered cells, all of which are derived from a single cell (Reynolds et al., Science 255:1707).

To initially test whether adult-derived Neural stem cells can survive in the microenvironment of very early embryogenesis, single spheres of Neural stem cells or numerous enzymatically dissociated single cells were initially aggregated with 8-cell compacted morulae and allowed to continue their development in vitro to the early blastocyst stage. Since the neural stem cells were cultured from Rosa26 mice which ubiquitously express *Escherichia coli*-derived β-galactosidase, these cells and their progeny could easily be identified after fixation and staining. In the early blastocysts, many of neural stem cells appeared to attach and proliferate on the external trophectoderm (FIG. 11A). However, a few of the cells were able to intermingle with the morulae cells and were found in the inner cell mass of the developing blastocyst (FIG. 11B). Since these Neural stem cells could successfully aggregate with 8 cell stage morulae and survive in the inner cell mass to the early blastocyst stage of development, it was plausible to assume that these cells may be able to contribute, at least in part, to the formation of the embryonic central nervous system or possibly to other embryonic tissues. A more efficient contribution of neural stem cells to the inner cell mass was acquired by microinjecting the cells directly into early blastocysts.

20f. Adult Neural Stem Cells can Contribute to the Generation of Chimeric Mouse Embryos To test the ability of adult neural stem cells to contribute to the generation of different tissues, C57/BL6 blastocysts injected with 10 to 20 single neural stem cells were transferred to foster mothers and allowed to develop until embryonic day 11. Embryos were fixed in paraformaldehyde and lacZ expression was assayed by X-gal histochemistry and immunohistochemistry with antibodies against β-galactosidase. Other embryos were used to detect the presence of β-galactosidase mRNA using RT-PCR.

Figure 11:
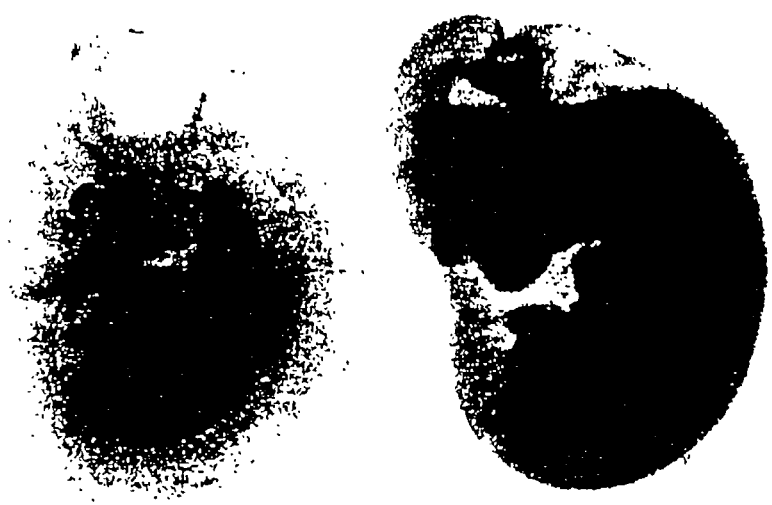
FIG. 11 shows the ability of ependymal CNS stem cells to contribute to the generation of multiple organs.
Figure 11:

Examination of E11 whole-mount embryos stained to detect the presence of β-galactosidase derived from the adult neural stem cells of the Rosa26 mice, revealed varying degrees of chimerism in the embryos analysed. Within litters, there was a large degree of variation in the degree of chimerism, and in all litters there were always several embryos which completely lacked lacZ expressing cells. Chimeric embryos were of similar size as non-chimeric embryos and did not display any overt anatomical abnormalities. One embryo displaying a high degree of chimerism is shown in FIG. 11 along with a wild-type C57/BL6 non-injected control. Superficial examination of the embryo derived from an injected blastocyst, reveals extensive contribution of the Rosa26-derived neural stem cells to the ventral spinal cord, the midbrain, the eyes, the heart and to many other internal organs and tissues. Embryos exhibiting less contribution from the Rosa26-derived neural stem cells, prunarily displayed staining either in the area of the midgut-hindgut junction or in the heart. A relatively low level of endogenous staining was frequently observed in the wild-type embryo in the area of the otic vesicles and the umbilical veins. However, no additional endogenous activity was seen in other areas of the wild-type embryos examined. The specificity of the X-gal staining in chimeric embryos was confirmed by overlapping inununohistochemical labelling with antisera against β-galactosidase. The areas which showed endogenous β-galactosidase like activity in wild type embryos, did not label with antisera against β-galactosidase.

Figure 12:
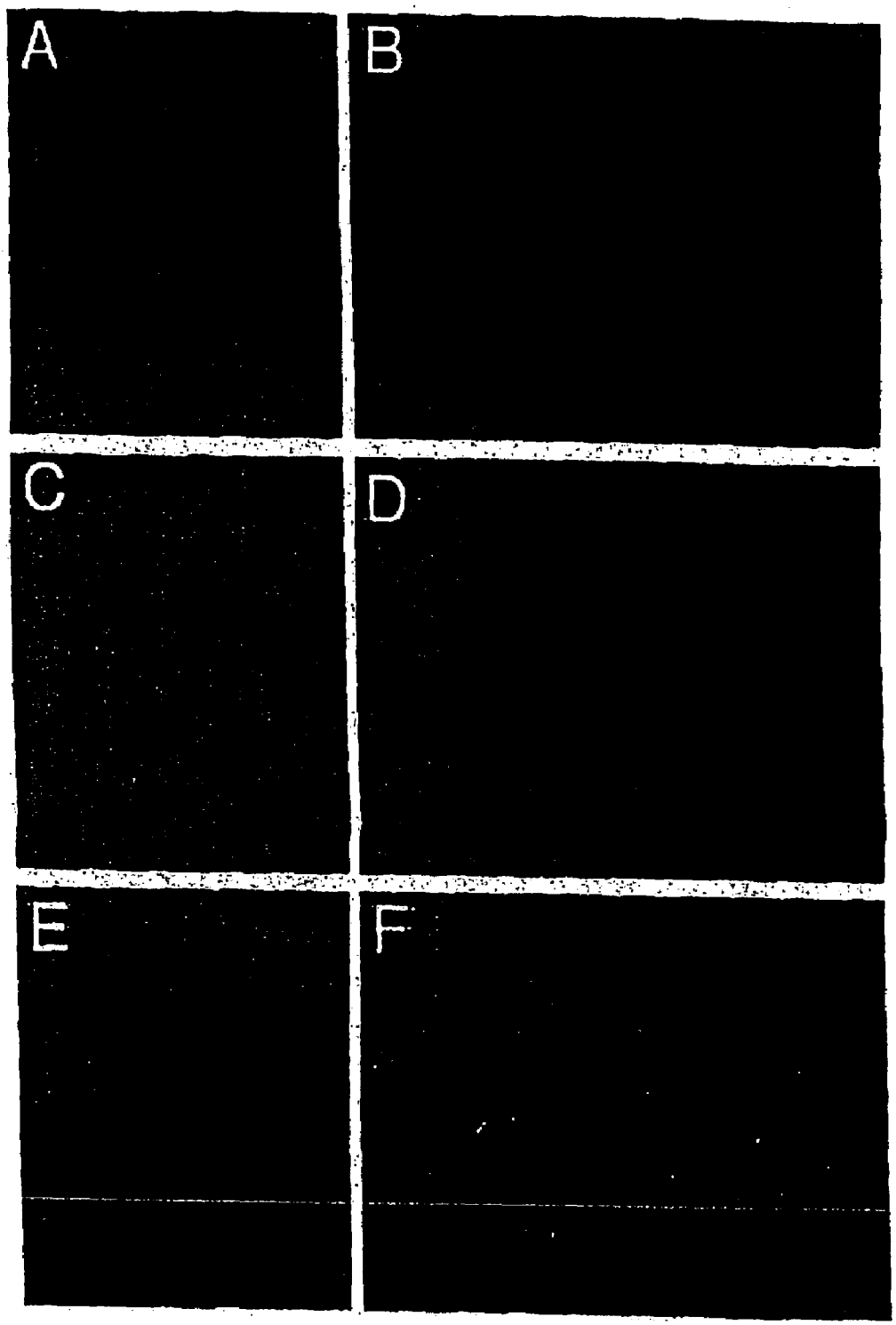
FIG. 12 presents thoracic contribution of adult neural ependymal stem cells to specialised tissues.

Moreover, to test for contribution of Rosa26 derived cells in yet an independent way, RT-PCR was used to assay for the presence of β-galactosidase mRNA in total RNA isolated from the E11 embryos injected with adult neural stem cells or from non-injected wild-type controls. Embryos used in this analysis were dissected transversely into three sections: head (including the brachial arches), thoracic area (below the brachial arches and above the umbilical cord) and the caudal region of the embryo (including the umbilical area, the hind limbs, and the tail). Oligonucleotide primers specific for the β-galactosidase gene were used to amplify the cDNA obtained from each of the embryonic sections. Two additional oligonucleotide primers specific for the detection of L19 mRNA, a ribosomal protein, were also added to the PCR reaction to serve as an internal control. β-galactosidase mRNA was not detected in samples taken from non-injected embryos, whereas a moderate signal was observed predominantly in the head and in the thoracic region of the embryos containing the heart and midgut. This distribution of lacZ expression was consistent with the pattern observed in whole-mount staining of other embryos to detect the expression pattern of the β-galactosidase gene product 20 g. Adult Neural Stem Cells Can Participate in the Generation of Tissues of All Germ Layers Examples of the chimeric embryo sections showing maximal levels of chineric contribution observed in tissues from embryos injected with the adult Neural stem cells, are shown in FIGS. 12 and 13, respectively. The adult Neural stem cells contribute significantly to some tissues of ectodermal origin in the E11 mouse embryo. Within the cranial region, contribution was most apparent in the ventral and medial regions of the spinal cord, the lamina terminalis of the Telencephalon, the infundibulum of the Diencephalon, the optic stalk, retinal layer and lens of the eye, the cochlea of the inner ear, and the nasal placodes. Within the thoracic region however, comparatively little contribution from the adult Neural stem cells can be observed in ectoderm-derived tissue, most notably to the epidermis.

A high chimeric contribution of the adult-derived Neural stem cells can also be observed in tissues derived from the definitive embryonic endoderm. This is prominently observed in the pharyngeal region, which includes the foiegut, tongue, the oral cavity, the pharyngeal pouches, and the thyroid gland. Within the thoracic region, contribution to tissues of endodermal origin was also significant in the esophagus, trachea, lung buds, stomach, intestine, pancreas, and liver.

Several tissues of mesodermal origin also exhibit a high level of contribution from the adult neural stem cells. These tissues included the notochord, the myocardium comprising the atrial and ventricular walls of the heart, the dorsal aorta, and the genital ridge primordium and mesonephric tubules. Here however, it is also important to note the comparatively reduced contribution of the adult-derived neural stem cells to the developing skeletal muscle and bone.

20 h. Differentiation to Tissue Specific Cell Types

To analyse whether the lacZ expressing cells derived from adult neural stem cell found in the chimeric embryos had differentiated into cell types typical of the tissue into which they had been integrated, we studied the expression of distinct cellular markers expressed by the cells normally comprising some of these tissues. We use double-immunohistochemical staining to demonstrate the overlapping expression of β-Galactosidase with monoclonal antibodies specific for Tuj1, HB9, Tyrosine hydroxylase (TH). Sonic hedgehog (Shh), Smooth muscle actin and Desmin (FIGS. 12 and 13). These antibodies detect β-Tubulin III (specific for axonal microtubules), motor neurons, dopaminergic neurons, Shh producing cells found in the ventral spinal cord, smooth muscle lining many arteries and veins and a intennediate filament found in cardiac and skeletal muscle, respectively. Additional antibodies are used to detect the co-localisation of insulin or glucagone secreting cells of the pancreas with that of β-Galactosidase.

Discussion

Cell loss is a common factor in many types of nervous system disorders. Distinct cell types are affected in different diseases, e.g. dopaminergic neurons in Parkinson's disease, motor neurons in amyotrophic lateral sclerosis and oligodendrocytes in multiple sclerosis. Several different cell types in a certain area can be affected in other situations, such as stroke or traumatic injury. Currently, no methods are available in clinical practice to stimulate generation of new cells in the nervous system. Transplantation of cells from human embryos or animals has been tested clinically with some encouraging results. However, these methods have several problems, mainly ethical and immunological, which makes it very unlikely that they will be used in any larger number of patients. The recent realisation that there is a population of multipotent stem cells in the adult central nervous system has fuelled hope that it may be possible to stimulate generation of new cells in the adult central nervous system from a patient's own stem cells. A few key questions have, however, remained unanswered and made it difficult to proceed in this field. The present identification of the stem cell has now made it possible to develop methods to purify these cells, study them quantitatively in vivo, genetically modify them and stimulate them with various pharmaceutical compounds in vitro and in vivo. Furthermore, the present invention provides evidence that the stem cells follow new migratory pathways to various neuroanatomical cell groups in the CNS and that they are able to transform into neurons in vivo. The invention also comprises an unbiased quantitative method to assess neurogenesis in various regions of the brain as well as techniques to analyse the total number of stem cells and their progeny migrating to various regions of the brain. Altogether, the developments provided by the present invention greatly increase the possibilities to develop strategies to stimulate generation of new cells in the central nervous system.

Altering the expression of genes in cells can make these cells produce a given protein of choice or can prevent the production of an unwanted protein. Manipulating the genes of cells in vitro or in vivo in accordance with the present invention may be beneficial in a wide variety of situations. For example, cells engineered to express a growth factor, cytokine, hormone or any other protein can be transplanted to individuals which may need continuous administration of such a protein to stimulate e.g. cell signalling or cell survival. The cells will thus serve as continuous administrators of a pharmaceutical substance. Cells for such use can be genetically tailored, by e.g. transfection with plasmid or viral vectors, or the cells can be taken from transgenic organisms. Transgenic organisms comprising cells according to the present invention are also within the scope of the present invention. Furthermore, gene expression can be altered in situ in an organism by inducing ectopic gene expression with plasmid or viral vectors as well as antisense DNA or RNA fragments. Under certain conditions, it may be valuable to use cells which lack a certain gene or produces lower levels of the gene product. For example, transplantation of cells or tissues between different individuals is limited by the expression of certain proteins on the surfaces of cells which induces the host immune system to reject the graft. This is a major problem, especially if the two individuals are of different species. One way to circumvent this problem is to generate genetically modified cells or animals that lack genes that induce rejection by a host immune system. Other important implications for manipulating gene expression in cells in vitro or in vivo include inducing differentiation of an undifferentiatied cell toward a certain cell fate or stimulating survival of the cell by suppressing intrinsic or extrinsic cell death signals. Furthermore, by introducing certain genes it is possible to immortalise cells and generate clonal cellines with special features. Since the identity and localisation of neural stem cells in the adult central nervous system has been unknown, it has previously been difficult to modify these cells genetically, especially in vivo. The invention of methods to purify stem cells in cell culture allows for all types of genetic manipulation, for example transfection of these cells with plasmid or viral expression vectors or purification of cells from transgenic organisms or suppression of gene expression with for example antisense DNA or RNA fragments. Localisation of the stem cell in vivo allows for alteration of gene expression in these cells in situ with for example viral vectors.

Above, it has also been demonstrated that stem cells from the adult brain can contribute to the formation of multiple tissues deriving from all geimlayers in chimeric mouse embryos. The progeny of the neural stem cells express tissue specific markers adequate for the tissues in which they integrate and which are not expressed in the nervous system. They integrate and differentiate in a functional way. Perhaps the most striking example of this is the frequent large contribution of neural stem cell progeny to the heart; the functionality of the cells was here obvious by a beating heart of apparent normal anatomy.

Epigenetic Control of Cell Differentiation

The cell fate of the progenitors arising from these stem cells in specific tissues may not be autonomously determined, but determined by the exposure of the cell to a reproducible set of extrinsic signals. In fact, in characterising the progeny of neural stem cells, there is mounting evidence that extrinsic growth factors can directly modify neural stem cell fate, biasing the subsequent differentiation. If clonal stem cell populations derived from the rodent hippocampus are transiently exposed to ciliary neurotrophic factor (CNTF), they produce astrocytes at the expense of neurons; if they are transiently exposed to thyroid hormone (T3), they produce oligodendrocytes at the expense of neurons. The same results are observed with embryonic or adult neural stem cells (Johe et al., Genes Dev. 10: 3129). These data suggest that growth factors directly affect stem cell fate, resulting in the production of progenitor cells committed to generating neurons, astrocytes, or oligodendrocytes. Similar results have been observed using clonally cultured neural crest cells; BMP2 induces autonomic neurons glial growth factor induces Schwann cell fate, and transforming growth factor-β (TGF-β) induces smooth-muscle differentiation (Shah et al., Cell 77: 349; Shah et al., Cell 85: 331). These data suggest that regional differences in gene expression may not lead to molecularly different populations of stem cells and that inherent differences in stem cell fate can easily modified be by exposure to extrinsic signals.

Do Adult Neural Stem Cells Lack Lineage Restriction or Do They Dedifferentiate?

Transplantation experiments in early embryos have defined time points when cells become restricted to certain lineages. The commitment to a certain fate is imposed by the expression of specific combinations of genes. In vitro experiments have demonstrated the potential of adult neural stem cells to generate neurons and glial cells. At first consideration it is therefore natural to assume that an adult neural stem cell need to undergo dedifferentiation in order to generate cells of a different lineage. However, it is noteworthy that many of the genes implied in giving a cell a certain lineage identity and restriction are expressed transiently during embryonic development. Expression of lineage determining genes may not be necessary after the development of a tissue since a stem cell population may be physically restrained to that particular tissue and the molecular environment may impel tissue specific fates on new cells. Thus, it is possible that the adult central nervous system stem cells have lost their neural commitment. Defining the multipotency of stem cells residing in the adult central nervous system, may help us to begin to understand the complex molecular events necessary for adult neural stem cells, or stem cells in general, to leave their quiescent state and enter a proliferative phase to produce progenitors with a determined cell fate. There are indications that other stem cell populations may have a broader differentiation potential in the adult than in the embryo. For example, hematopoietic stem cells transplanted to the brain can generate astrocytes. This raises the possibility that stem cells in different adult tissues may be very similar and have a potential close to embryonic stem cells. In fact, it is possible that there is only one fundamental stem cell population that exists in the adult organism.

To more directly address the cellular potency of the neural stem cells derived from the lateral ventricular wall of the adult brain, we have placed these cells into the early blastocyst microenvironment and have found that these cells contribute to numerous organs and tissues that are originally derived from all three germ layers during embryonic development.

In summary, the present invention will make it possible to develop new treatment strategies in diverse diseases of the CNS, not only in diseases with a slow progression of the neurodegeneration (including Alzheimer's disease, Parkinson's disease, amyotrophic lateral sclerosis, multiple sclerosis) but also in clinical situations of acute trauma to the head or spinal cord as well as in cerebrovascular diseases. Our finding that stem cells may transform into several different neuronal phenotypes (dopanine neurons, GABA-neurons, serotonin neurons) as well as into completely different tissue types open up possible applications beyond the above mentioned diseases, where cell loss is central to the development of the disease, into possible new areas, including depression and other mental disorders, as well as cardiac surgery.

Various publications are cited herein, the disclosures of which are incorporated by reference in their entireties. The present invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

The invention claimed is:

1. An isolated ependymal neural CNS stem cell from a mammal, wherein said stem cell expresses Notch 1 and one or more other cell surface proteins, wherein the cell surface protein is selected from the group consisting of Notch 2, Notch 3, CAR, and CFTR.

2. An isolated ependymal neural CNS stem cell from a mammal, wherein said stem cell comprises one or more cilia, and expresses Notch 1 and one or more other cell surface proteins, wherein the cell surface protein is selected from the group consisting of Notch 2, Notch 3, CAR, and CFTR.

3. The stem cell of claim 1 or 2, wherein the cell surface protein is Notch 2.

4. The stem cell of claim 1 or 2, wherein the cell surface protein is Notch 3.

5. The stem cell of claim 1 or 2, wherein the cell surface protein is CAR.

6. The stem cell of claim 1 or 2, wherein the cell surface protein is CFTR.

7. The stem cell of claim 1 or 2, wherein the stem cell is genetically manipulated.

8. A cell preparation comprising ependymal neural CNS stem cells from a mammal, wherein said preparation comprises at least 50% ependymal neural CNS stem cells.

9. A cell preparation comprising ependymal neural CNS stem cells from a mammal, wherein said preparation comprises at least 80% ependymal neural CNS stem cells.

10. A cell preparation comprising ependymal neural CNS stem cells from a mammal, wherein said preparation comprises at least 90% ependymal neural CNS stem cells.

11. The cell preparation of claim 8, 9, or 10, wherein at least 4% of the stem cells are active stem cells that undergo self-renewal and that are multipotent.

12. A method of isolating ependymal neural CNS stem cells from a mammal, which method comprises the steps of:
   (a) screening single cells obtained by dissociating CNS tissue from said mammal for cells expressing Notch 1 and one or more other cell surface proteins, wherein the cell surface protein is selected from the group consisting of Notch 2, Notch 3, CAR, and CFTR; and
   (b) recovering the cells expressing Notch 1 and one or more other cell surface proteins, wherein the cell surface protein is selected from the group consisting of Notch 2, Notch 3, CAR, and CFTR,
   wherein the cells recovered in step (b) are the ependymal neural CNS stem cells.

13. A method of isolating ependymal neural CNS stem cells from a mammal, which method comprises the steps of:
   (a) screening single cells obtained by dissociating CNS tissue from said mammal for cells that comprise one or more cilia and that express Notch 1 and one or more other cell surface proteins, wherein the cell surface protein is selected from the group consisting of Notch 2, Notch 3, CAR, and CFTR; and
   (b) recovering the cells that comprise at least one cilium, and that express Notch 1 and one or more other cell surface proteins, wherein the cell surface protein is selected from the group consisting of Notch 2, Notch 3, CAR, and CFTR,
   wherein the cells recovered in step (b) are the ependymal neural CNS stem cells.

14. The method of claim 12 or 13, said method further comprising obtaining CNS tissue from said mammal, said CNS tissue comprising lateral ventricles, and dissecting out the lateral walls of the lateral ventricles prior to said screening step.

15. The method of claim 12 or 13, said method further comprising culturing the stem cells in a medium, said medium comprising EGF and/or FGF.

16. The method of claim 12 or 13, said method further comprising labeling ependymal cells with a label, and screening the cells for the label.

17. The method of claim 16, wherein the label is DiI.

18. The method of claim 12 or 13, wherein said CNS tissue is dissociated by one or more hydrolyzing enzymes or by kynurenic acid.

19. The method of claim 18, wherein the hydrolyzing enzyme is collagenase, trypsin, or hyaluronidase.

20. The method of claim 12 or 13, wherein the cell surface protein is Notch 2.

21. The method of claim 12 or 13, wherein the cell surface protein is Notch 3.

22. The method of claim 12 or 13, wherein the cell surface protein is CAR.

23. The method of claim 12 or 13, wherein the cell surface protein is CFTR.

24. A method according to any of claims 12 or 13, wherein said mammal is a human.

25. A composition comprising the following ingredients:
   (i) an isolated ependymal neural CNS stem cell from a mammal, wherein said stem cell expresses Notch 1 and one or more other cell surface proteins, wherein the cell surface protein is selected from the group consisting of Notch 2, Notch 3, CAR, and CFTR; and (ii) a pharmaceutically acceptable carrier.

26. A composition comprising the following ingredients:
   (i) an isolated ependymal neural CNS stem cell from a mammal, wherein said stem cell comprises one or more cilia, and expresses Notch 1 and one or more other cell surface proteins, wherein the cell surface protein is selected from the group consisting of Notch 2, Notch 3, CAR, and CFTR; and (ii) a pharmaceutically acceptable carrier.

* * * * *

SEQUENCE LISTING

<160> NUMBER OF SEQ ID NOS: 4

<210> SEQ ID NO 1
<211> LENGTH: 24
<212> TYPE: DNA
<213> ORGANISM: Artificial Sequence
<220> FEATURE:
<223> OTHER INFORMATION: PCR-primers for the beta-galactosidase gene from
      E. coli.

<400> SEQUENCE: 1
ttggagtgac ggcagttatc tgga                                              24

<210> SEQ ID NO 2
<211> LENGTH: 24
<212> TYPE: DNA
<213> ORGANISM: Artificial Sequence
<220> FEATURE:
<223> OTHER INFORMATION: PCR-primers for the beta-galactosidase gene from
      E. coli.

<400> SEQUENCE: 2
tcaaccaccg cacgatagag attc                                              24

<210> SEQ ID NO 3
<211> LENGTH: 27
<212> TYPE: DNA
<213> ORGANISM: Artificial Sequence
<220> FEATURE:
<223> OTHER INFORMATION: PCR-primers for the beta-galactosidase gene from
      E. coli.

<400> SEQUENCE: 3
ccttggacag agtcttgatg atctcct                                           27

<210> SEQ ID NO 4
<211> LENGTH: 27
<212> TYPE: DNA
<213> ORGANISM: Artificial Sequence
<220> FEATURE:
<223> OTHER INFORMATION: PCR-primers for the beta-galactosidase gene from
      E. coli.

<400> SEQUENCE: 4
cttctcagga gataccggga atctaag                                           27